(12) United States Patent
Purdy et al.

(10) Patent No.: US 10,363,185 B2
(45) Date of Patent: Jul. 30, 2019

(54) SYSTEM AND METHOD FOR OFF-LOADING OF THE BODY IN THE PRONE POSITION AND FOR PATIENT TURNING AND REPOSITIONING

(71) Applicant: MÖLNLYCKE HEALTH CARE US, LLC, Norcross, GA (US)

(72) Inventors: William Purdy, White Plains, NY (US); Robert Purdy, Bedford, NY (US)

(73) Assignee: MÖLNLYCKE HEALTH CARE AB, Gothenburg (SE)

( * ) Notice: Subject to any disclaimer, the term of this patent is extended or adjusted under 35 U.S.C. 154(b) by 136 days.

(21) Appl. No.: 14/845,062

(22) Filed: Sep. 3, 2015

(65) Prior Publication Data
US 2016/0067126 A1    Mar. 10, 2016

Related U.S. Application Data

(60) Provisional application No. 62/045,788, filed on Sep. 4, 2014.

(51) Int. Cl.
*A61G 7/057* (2006.01)
*A61G 7/00* (2006.01)
(Continued)

(52) U.S. Cl.
CPC ........ *A61G 7/05738* (2013.01); *A61B 6/0485* (2013.01); *A61G 7/001* (2013.01);
(Continued)

(58) Field of Classification Search
CPC ...... A61G 7/001; A61G 7/057; A61G 7/1021; A61G 7/1025; A61G 7/05738;
(Continued)

(56) References Cited

U.S. PATENT DOCUMENTS

| 1,334,901 A | 3/1920 | Higdon |
| 2,466,142 A | 4/1949 | Yost |

(Continued)

FOREIGN PATENT DOCUMENTS

| CN | 201208361 | 3/2009 |
| DE | 4447431 | 6/1996 |

(Continued)

OTHER PUBLICATIONS

U.S. Appl. No. 13/834,911, Non-Final Office Action, dated May 23, 2016, 15 pages.

(Continued)

*Primary Examiner* — Robert G Santos
*Assistant Examiner* — David R Hare
(74) *Attorney, Agent, or Firm* — Kilpatrick Townsend & Stockton LLP

(57) ABSTRACT

The present invention relates to a system and method for support and off-loading. The system includes an inner bladder filled with a flowable composition. An outer bladder filled with a flowable composition is positioned adjacent to the inner bladder. The composition of the inner bladder has greater flow characteristics than the composition of the outer bladder. The inner bladder micro-contours to the received body part and the outer bladder macro-contours to the inner bladder after the inner bladder is micro-contoured to the received body part. Alternatively, the system provides a pair of ultra low pressure plenums and a positioner. The patient body size and size and corresponding surface area of the positioner control the amount of gas which is displaced evenly against the walls of the ultra low pressure plenums.

20 Claims, 18 Drawing Sheets

(51) Int. Cl.
*A61G 7/10* (2006.01)
*A61B 6/04* (2006.01)

(52) U.S. Cl.
CPC ......... *A61G 7/057* (2013.01); *A61G 7/05753* (2013.01); *A61G 7/05769* (2013.01); *A61G 7/1021* (2013.01); *A61G 7/1025* (2013.01); *A61B 6/0421* (2013.01)

(58) Field of Classification Search
CPC ............ A61G 7/05746; A61G 7/05753; A61G 7/05769; A61G 7/05776; A61B 6/0485; A61B 6/0421
See application file for complete search history.

(56) References Cited

U.S. PATENT DOCUMENTS

| | | | |
|---|---|---|---|
| 2,489,828 A | 11/1949 | Springer | |
| 2,748,399 A | 6/1956 | Rockoff | |
| 3,158,875 A | 12/1964 | Fletcher | |
| 3,212,497 A * | 10/1965 | Dickinson | A61B 6/0421 128/DIG. 20 |
| 3,331,087 A | 7/1967 | Barlow | |
| 3,526,908 A | 9/1970 | Davis | |
| 3,762,404 A * | 10/1973 | Sakita | A43B 17/035 128/DIG. 20 |
| 3,829,914 A | 8/1974 | Treat | |
| 3,840,920 A * | 10/1974 | Voelker | A47C 20/025 297/284.3 |
| 3,849,813 A | 11/1974 | Neilson | |
| 3,968,530 A * | 7/1976 | Dyson | A47C 27/085 5/648 |
| 4,005,498 A | 2/1977 | Starr et al. | |
| 4,024,861 A | 5/1977 | Vincent et al. | |
| 4,045,830 A * | 9/1977 | Loeb | A61B 1/00 264/571 |
| 4,051,565 A | 10/1977 | Berge | |
| 4,139,920 A * | 2/1979 | Evans | A47C 3/16 5/420 |
| 4,211,218 A | 7/1980 | Kendrick | |
| 4,213,213 A * | 7/1980 | Burnett | A47C 7/46 297/284.1 |
| 4,272,856 A * | 6/1981 | Wegener | A61G 1/00 180/116 |
| 4,347,213 A * | 8/1982 | Rogers, Jr. | A47C 7/46 264/102 |
| 4,371,997 A * | 2/1983 | Mattson | A47C 27/081 297/DIG. 3 |
| 4,428,087 A * | 1/1984 | Horn | A47C 27/081 5/638 |
| 4,472,847 A | 9/1984 | Gammons et al. | |
| 4,517,690 A | 5/1985 | Wegener | |
| 4,566,445 A | 1/1986 | Jelsma et al. | |
| 4,665,908 A | 5/1987 | Calkin et al. | |
| 4,736,474 A | 4/1988 | Moran et al. | |
| 4,741,057 A | 5/1988 | Pasca et al. | |
| 4,977,629 A | 12/1990 | Jones | |
| 5,009,318 A * | 4/1991 | Lepinoy | A61G 7/05753 128/DIG. 20 |
| 5,044,031 A | 9/1991 | Sherwood et al. | |
| 5,060,324 A | 10/1991 | Marinberg et al. | |
| 5,065,464 A | 11/1991 | Blanchard et al. | |
| 5,067,189 A | 11/1991 | Weedling et al. | |
| 5,092,007 A * | 3/1992 | Hasty | A61G 7/001 5/691 |
| 5,103,517 A * | 4/1992 | Krouskop | A61G 7/05753 5/702 |
| 5,103,518 A | 4/1992 | Gilroy et al. | |
| 5,121,756 A * | 6/1992 | Koledin | A61F 5/05833 128/DIG. 20 |
| 5,243,722 A | 9/1993 | Ignaty | |
| 5,329,655 A * | 7/1994 | Garner | A61G 7/1026 5/502 |
| 5,421,874 A * | 6/1995 | Pearce | A43B 5/0405 106/122 |
| 5,489,259 A | 2/1996 | Jacobs et al. | |
| 5,549,743 A | 8/1996 | Pearce | |
| 5,556,169 A * | 9/1996 | Parrish | A42B 3/121 297/452.28 |
| 5,626,150 A | 5/1997 | Johnson et al. | |
| 5,626,657 A | 5/1997 | Pearce | |
| 5,708,999 A | 1/1998 | Priolo et al. | |
| 5,794,289 A | 8/1998 | Wortman et al. | |
| 5,806,796 A | 9/1998 | Healey | |
| 5,832,550 A * | 11/1998 | Hauger | A61B 5/1078 5/411 |
| 5,869,164 A | 2/1999 | Nickerson et al. | |
| 5,901,392 A | 5/1999 | Hsuan-Chi | |
| 5,966,754 A * | 10/1999 | Schuster | A61G 7/103 5/625 |
| 5,966,763 A | 10/1999 | Thomas et al. | |
| 6,020,055 A | 2/2000 | Pearce | |
| 6,073,291 A | 6/2000 | Davis | |
| 6,110,006 A | 8/2000 | Chen | |
| 6,119,292 A | 9/2000 | Haas | |
| 6,128,796 A | 10/2000 | McCormick et al. | |
| 6,145,143 A | 11/2000 | Hicks et al. | |
| 6,151,739 A | 11/2000 | Meyer et al. | |
| 6,154,900 A | 12/2000 | Shaw | |
| 6,158,070 A * | 12/2000 | Bolden | A61G 7/05746 5/689 |
| 6,175,980 B1 | 1/2001 | Gaither et al. | |
| 6,192,537 B1 * | 2/2001 | Miki | A47C 27/086 5/689 |
| 6,197,099 B1 | 3/2001 | Pearce | |
| 6,209,159 B1 | 4/2001 | Murphy et al. | |
| 6,209,962 B1 * | 4/2001 | Sobel | A47C 3/16 297/452.17 |
| 6,226,820 B1 * | 5/2001 | Navarro | A47C 27/085 5/654 |
| 6,254,959 B1 * | 7/2001 | Hirano | A61G 5/1043 428/407 |
| 6,318,372 B1 | 11/2001 | Hiebert et al. | |
| 6,327,724 B1 * | 12/2001 | Sharrock | A61G 7/07 5/630 |
| 6,343,385 B1 | 2/2002 | Katz | |
| 6,351,863 B1 | 3/2002 | Meyer et al. | |
| 6,357,066 B1 * | 3/2002 | Pierce | A61B 6/0442 5/710 |
| 6,381,787 B1 | 5/2002 | Rogone et al. | |
| 6,397,419 B1 | 6/2002 | Mechache | |
| 6,421,859 B1 | 7/2002 | Hicks et al. | |
| 6,425,399 B1 | 7/2002 | Hoster et al. | |
| 6,498,198 B2 | 12/2002 | Pearce | |
| 6,499,166 B1 * | 12/2002 | Jones | A47C 20/048 5/615 |
| 6,588,511 B1 | 7/2003 | Kriesel et al. | |
| 6,604,252 B1 | 8/2003 | Lee et al. | |
| 6,701,544 B2 | 3/2004 | Heimbrock | |
| 6,718,584 B2 | 4/2004 | Rabaiotti et al. | |
| 6,823,549 B1 | 11/2004 | Hampton et al. | |
| 6,857,151 B2 | 2/2005 | Jusiak et al. | |
| 6,896,065 B2 | 5/2005 | Kriesel et al. | |
| 6,986,170 B2 | 1/2006 | Nelson | |
| 7,007,330 B2 | 3/2006 | Kuiper et al. | |
| 7,020,912 B2 * | 4/2006 | Berge | A61G 7/1026 5/482 |
| 7,032,261 B2 | 4/2006 | Heimbrock | |
| 7,055,190 B2 | 6/2006 | Barth et al. | |
| 7,065,815 B2 | 6/2006 | Buchanan | |
| 7,080,422 B2 | 7/2006 | Ben-Levi | |
| 7,146,660 B2 | 12/2006 | Heimbrock | |
| 7,200,956 B1 | 4/2007 | Kotha et al. | |
| 7,243,382 B2 | 7/2007 | Weedling et al. | |
| 7,266,852 B2 | 9/2007 | Davis | |
| 7,340,785 B2 | 3/2008 | Weedling et al. | |
| 7,360,543 B1 | 4/2008 | Coleman et al. | |
| 7,415,738 B2 | 8/2008 | Weedling et al. | |
| 7,424,760 B2 | 9/2008 | Chaffee et al. | |
| 7,464,422 B2 | 12/2008 | Townsend | |
| 7,467,431 B2 | 12/2008 | Weedling et al. | |

(56) References Cited

U.S. PATENT DOCUMENTS

| | | | |
|---|---|---|---|
| 7,559,103 B2 | 7/2009 | Barth et al. | |
| 7,565,710 B2 | 7/2009 | Chambers et al. | |
| 7,591,029 B2 | 9/2009 | Weedling et al. | |
| 7,650,654 B2 | 1/2010 | Lambarth et al. | |
| 7,681,262 B2 | 3/2010 | Weedling et al. | |
| 7,725,963 B2 | 6/2010 | Johnson | |
| 7,739,758 B2 | 6/2010 | Weedling et al. | |
| 7,832,039 B2 | 11/2010 | Chambers et al. | |
| 7,900,299 B2 | 3/2011 | Weedling et al. | |
| 7,904,971 B2 | 3/2011 | Doria et al. | |
| 7,945,979 B1 | 5/2011 | Lin | |
| 7,975,331 B2* | 7/2011 | Flocard | A47C 21/044 5/423 |
| 8,001,636 B2 | 8/2011 | Nissen et al. | |
| 8,096,003 B2* | 1/2012 | Schuster | A61G 7/1032 5/627 |
| 8,171,585 B2* | 5/2012 | Mead | A41D 31/0044 2/455 |
| 8,191,188 B2 | 6/2012 | Kaplan et al. | |
| 8,234,727 B2 | 8/2012 | Schreiber et al. | |
| 8,261,388 B1 | 9/2012 | Gill et al. | |
| 8,302,222 B2 | 11/2012 | Jasani | |
| 8,387,187 B2* | 3/2013 | Hieronimi | A61B 6/0428 5/657 |
| 8,418,296 B1 | 4/2013 | Hanlon et al. | |
| 8,555,890 B2* | 10/2013 | Hiebert | A61G 13/121 128/845 |
| 8,566,977 B2 | 10/2013 | Davis | |
| 8,607,385 B2* | 12/2013 | Isham | A61G 13/123 5/621 |
| 8,661,580 B2 | 3/2014 | Giap | |
| 8,667,631 B2 | 3/2014 | Coates et al. | |
| 8,671,479 B2* | 3/2014 | Huttner | A61G 7/05753 5/630 |
| 8,690,807 B2* | 4/2014 | Hiebert | A61F 5/05833 128/845 |
| 8,701,225 B1 | 4/2014 | Latiff | |
| 8,756,725 B2 | 6/2014 | Piegdon et al. | |
| 8,789,533 B2 | 7/2014 | Steffens et al. | |
| 8,850,634 B2 | 10/2014 | Ponsi et al. | |
| 8,858,478 B2 | 12/2014 | Purdy et al. | |
| 8,898,833 B2 | 12/2014 | Coates et al. | |
| 8,984,681 B2 | 3/2015 | Ponsi | |
| 9,149,402 B2 | 10/2015 | Gomez et al. | |
| 9,445,933 B2* | 9/2016 | Williams | A61F 5/05833 |
| 9,504,621 B2* | 11/2016 | Purdy | |
| 9,782,313 B2* | 10/2017 | Hindson | A61G 7/1032 |
| 2002/0104535 A1 | 8/2002 | Biondo et al. | |
| 2002/0144343 A1 | 10/2002 | Kuiper et al. | |
| 2003/0192123 A1 | 10/2003 | Chaffee | |
| 2003/0200611 A1 | 10/2003 | Chaffee | |
| 2004/0083550 A1 | 5/2004 | Graebe, Jr. et al. | |
| 2005/0028273 A1 | 2/2005 | Weedling et al. | |
| 2006/0037136 A1 | 2/2006 | Weedling et al. | |
| 2006/0179577 A1 | 8/2006 | Chaffee | |
| 2007/0083995 A1* | 4/2007 | Purdy | A61G 7/05753 5/702 |
| 2007/0118993 A1 | 5/2007 | Bates | |
| 2007/0283496 A1 | 12/2007 | Skripps et al. | |
| 2008/0083067 A1 | 4/2008 | Wheeldon-Glazener | |
| 2008/0134442 A1 | 6/2008 | Hui | |
| 2008/0201855 A1 | 8/2008 | Groves et al. | |
| 2009/0106893 A1 | 4/2009 | Blevins | |
| 2009/0271928 A1 | 11/2009 | Tishby et al. | |
| 2010/0096419 A1 | 4/2010 | Stephens et al. | |
| 2010/0170037 A1 | 7/2010 | Fletcher et al. | |
| 2011/0220695 A1 | 9/2011 | Saunders et al. | |
| 2011/0241300 A1 | 10/2011 | Schioler et al. | |
| 2011/0271444 A1 | 11/2011 | Davis | |
| 2012/0011658 A1 | 1/2012 | Weedling et al. | |
| 2012/0049605 A1 | 3/2012 | Sanefuji et al. | |
| 2012/0079656 A1 | 4/2012 | Lewis et al. | |
| 2012/0186587 A1 | 7/2012 | Steffens et al. | |
| 2012/0284923 A1 | 11/2012 | Jensen et al. | |
| 2012/0311781 A1 | 12/2012 | Purdy et al. | |
| 2012/0311787 A1 | 12/2012 | Purdy et al. | |
| 2012/0311788 A1 | 12/2012 | Jackson et al. | |
| 2013/0061396 A1 | 3/2013 | Lafleche et al. | |
| 2013/0145559 A1 | 6/2013 | Purdy et al. | |
| 2013/0152950 A1* | 6/2013 | Giap | A61F 5/3776 128/872 |
| 2013/0180046 A1 | 7/2013 | Davis et al. | |
| 2013/0198950 A1 | 8/2013 | Purdy et al. | |
| 2013/0205495 A1 | 8/2013 | Ponsi et al. | |
| 2013/0230685 A1* | 9/2013 | Smith | A47G 9/1027 428/71 |
| 2013/0276235 A1 | 10/2013 | Kenalty et al. | |
| 2013/0340770 A1 | 12/2013 | Starr et al. | |
| 2014/0007353 A1 | 1/2014 | Stryker et al. | |
| 2014/0041114 A1 | 2/2014 | Davis | |
| 2014/0075673 A1 | 3/2014 | Weedling et al. | |
| 2015/0052685 A1 | 2/2015 | Bhat et al. | |
| 2015/0101126 A1 | 4/2015 | Reiners et al. | |
| 2015/0128341 A1 | 5/2015 | Kuiper | |
| 2015/0135443 A1 | 5/2015 | Cortez | |
| 2015/0157521 A1 | 6/2015 | Williams et al. | |
| 2015/0238378 A1 | 8/2015 | Bhat et al. | |
| 2015/0290848 A1 | 10/2015 | Sanefuji et al. | |

FOREIGN PATENT DOCUMENTS

| | | |
|---|---|---|
| EP | 0821928 | 2/1998 |
| GB | 2300845 A1 | 11/1996 |
| IN | 5020/DELNP/2006 | 8/2007 |
| JP | 58160035 | 10/1983 |
| WO | 2001037774 | 5/2001 |
| WO | 2014043525 | 3/2014 |
| WO | 2015057775 | 4/2015 |
| WO | 2015128618 | 9/2015 |
| WO | 2015130703 | 9/2015 |
| WO | 2016037108 | 3/2016 |

OTHER PUBLICATIONS

U.S. Appl. No. 13/493,641, Non-Final Office Action, dated Jun. 1, 2016, 15 pages.

Blue Chip Medical Products, Inc., Power Pro Elite® Mattress System—Model 9500, retrieved from the Internet at https://web.archive.org/web/20100501171106/http://www.bluechipmedical.com/mattress-systems/air-mattress/power-pro-elite, at least as early as May 1, 2010, 4 pages.

EZ Way, Inc., EZ Matt, retrieved from the Internet at https://web.archive.org/web/20090202082654/http://ezlifts.com/products/product_details.cfm?ProductID=27, at least as early as Feb. 2, 2009, 1 page.

Hill-Rom®, AirPal® Patient Air Lift, retrieved from the Internet at https://web.archive.org/web/20101015045524/http://www.hill-rom.com/usa/AirPal.htm, at least as early as Oct. 15, 2010, 1 page.

Hill-Rom®, AIRPAL® Patient Transfer System, Dec. 22, 2008, http://www.discovermymobility.com/store/patient-lifts/hill-rom/hill-rom-patient-transfer-system.pdf, 2 pages.

HoverTech, HoverMatt® Air Transfer System, retrieved from the Internet at https://web.archive.org/web/20110208085745/http://www.hovermatt.com/reusable, at least as early as Feb. 8, 2011, 1 page.

McAuley Medical, Inc., AirSlide for lateral transfer in-service video, uploaded to Internet on Mar. 14, 2009, https://www.youtube.com/watch?v=u0tftK_4qOE.

MDI—Medical Devices International, EMS IMMOBILE-VAC™, retrieved from the Internet at https://web.archive.org/web/20081120122715/http://www.mdimicrotek.com/prod_ems-immobilevac.htm, at least as early as Nov. 20, 2008, 5 pages.

Smart Medical Technology, Inc.®, Liftaem™—Revolutionary Lateral Patient Transfer Device, uploaded to Internet on Apr. 4, 2008, https://www.youtube.com/watch?v=K7_9XA-dS5k.

Stryker, Stryker Glide Lateral Air Transfer System, 2009, https://www.stryker.com/stellent/groups/public/documents/web_content/glidespecsheetrevd.pdf, 2 pages.

Sundance Enterprises, Inc., Healthcare Products, The DAP 210 Static Overlay Mattress, retrieved from the Internet at https://web.

(56) References Cited

OTHER PUBLICATIONS archive.org/web/20061014205929/http://sundancesolutions.com/dap210.php, at least as early as Oct. 14, 2006, 2 pages.
Sundance Enterprises, Inc., Healthcare Products, The DAP Series, Static Air Support System and Fluidized Positioners, retrieved from the Internet at https://web.archive.org/web/20061013091949/http://sundancesolutions.com/healthcareproducts.php, at least as early as Oct. 13, 2006, 1 page.
International Patent Application No. PCT/US2015/048642, International Search Report and Written Opinion, dated Dec. 2, 2015, 8 pages.
U.S. Appl. No. 13/493,582, Non-Final Office Action, dated Aug. 26, 2015, 10 pages.
U.S. Appl. No. 13/493,582, Non-Final Office Action, dated Feb. 29, 2016, 17 pages.
U.S. Appl. No. 13/834,911, Non-Final Office Action, dated Aug. 25, 2015, 8 pages.
U.S. Appl. No. 13/493,641, Non-Final Office Action, dated Sep. 9, 2015, 7 pages.
AU2015311732, "First Examiner Report", dated Sep. 27, 2017, 4 pages.
U.S. Appl. No. 13/493,641, "Final Office Action", dated Aug. 2, 2017, 8 pages.
U.S. Appl. No. 13/493,641, "Notice of Allowance", dated Sep. 26, 2017, 11 pages.
European Application No. 15837218.5, Office Action dated Apr. 6, 2018, 5 pages.
EP15837218.5, "Extended European Search Report", dated Mar. 30, 2017, 9 pages.
AU2015311732, "Notice of Acceptance", dated Oct. 9, 2018, 3 pages.
CN201580047648.7, "Office Action", dated Sep. 3, 2018, 8 pages.

\* cited by examiner

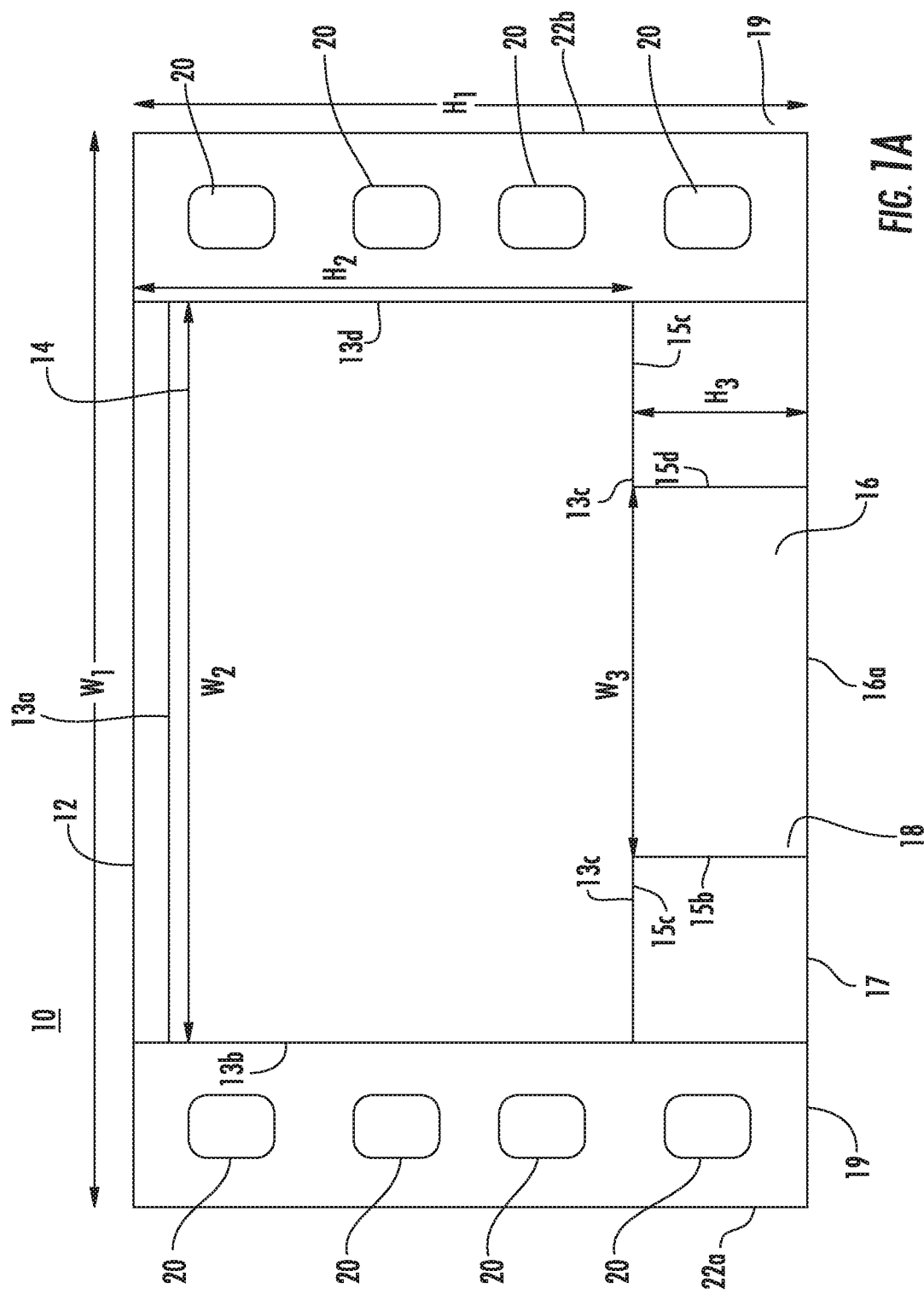

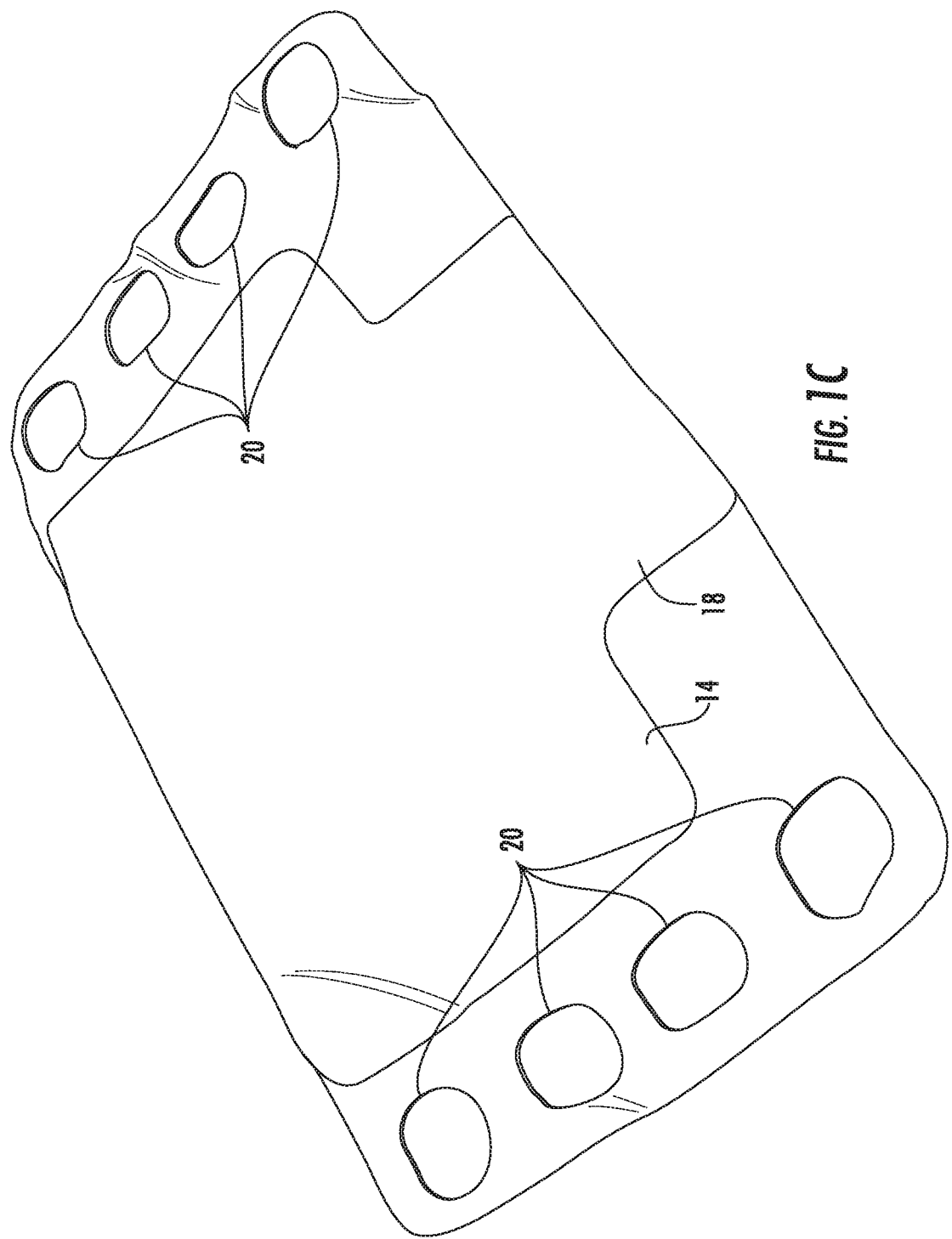

SYSTEM AND METHOD FOR OFF-LOADING OF THE BODY IN THE PRONE POSITION AND FOR PATIENT TURNING AND REPOSITIONING

BACKGROUND OF THE INVENTION

Field of the Invention

The present invention relates to a patient support which can be used in a bed or flat surface and in particular to a system and method for support of the body, in particular in the prone position, which can also be used for turning and repositioning of a patient in a bed or on a flat surface.

Description of Related Art

Hospital bed and other patient static air and dynamic air supports are known. Typically, such patient supports are used to provide a support surface for patients or other individuals for treatment, recuperation, or rest and prevention of skin breakdown.

U.S. Pat. No. 3,762,404 describes a positioning aid for restraining and immobilizing a part of the body of a medical patient including an air-tight flexible bag and deformable spherulic beads of expanded polystyrene are confined in the bag. A valve communicates with the interior of the bag for evacuating air therefrom. The bag becomes rigid upon evacuation of air from the bag.

It is desirable to provide an improved support off-loading the patient in the prone position including bony prominences.

SUMMARY OF THE INVENTION

The present invention relates to a system and method for body support and off-loading. It is optimal to barely elevate the body in a prone position from the surface of the bed. In the prone position, the body is laying face forward towards the support surface. The system provides a support including a first ultra low pressure plenum, a second ultra low pressure plenum and a positioner. Each of the ultra low pressure plenums can include one or more air chambers. Each air chamber is filled at a predetermined low pressure for distributing pressure along the length of the ultra low pressure plenum, but not providing significant elevation of a received body part by itself.

A cover can be received over the ultra low plenums. The cover can include a retaining member for receiving the positioner. The cover can include a temperature regulating material for keeping the received body part in an optimal range of skin temperature to keep comfortable longer. In one embodiment, a phase change material can be used for adjusting the temperature of the system to adapt to temperature changes of the body.

The positioner includes a bladder preferably filled with a fluidized particulate material with sufficient size and shape to displace an amount of air in the support to offload pressure being from a received body part, such as, but not limited to, bony prominences of which contact a surface when the body is positioned in a prone position and when the body is turned to other positions. The surface area of the positioner provides greater positive air displacement in the ultra low pressure plenums than would occur from the body part of the patient by itself. In one embodiment, the positioner can have a greater width than the patient. The positioner provides three dimensional movement. Preferably, the positioner has little or no flow characteristics unless an outside force is applied other than gravity. The positioner can displace and contour three dimensionally as though it was fluid while not having flow characteristics that would result in migration of the medium under the force of gravity. The positioner can provide three dimensional contouring. The positioner can be shaped as a pad.

In one embodiment, the first ultra low pressure plenum includes a lower bladder section having a smaller width dimension than an upper bladder section. The air chambers of the lower bladder section and the upper bladder section being in air communication with one another. Air is communicated within the upper bladder section and lower bladder section through air displacement. The patient body size and size and corresponding surface area of the positioner control the amount of air which is displaced evenly against the walls of the first ultra low pressure plenum. A second ultra low pressure plenum is placed under the first ultra low pressure plenum. Alternatively, the second ultra low pressure plenum can be placed on top of the first ultra low pressure plenum. The second ultra low pressure plenum can have a size and shape identical or substantially similar to the upper bladder section of the first ultra low pressure plenum. The positioner is placed beneath or on top of both the first ultra low pressure plenum and the second ultra low pressure plenum or at other positions of the first ultra low pressure plenum and the second low pressure plenum or in combination one or more additional positioners. In one embodiment, the positioner displaces air in both the first ultra low pressure plenum and the second ultra low pressure plenum to off-load the body and allow the lungs to expand in a prone position of the body. In one embodiment, the positioner can be positioned at one of outer walls of the first ultra low pressure plenum to push air away from the outer wall, thereby aiding in turning of a patient.

For example, the support can be used to allow a patient to be supported in the prone position for off-loading the body from the collar bone to the knees to aid in treating advanced respiratory distress.

The combination of the first and second ultra low pressure plenums and positioner, including a fluidized medium, creates sufficient support of the received body part while responding to normal patient movement. The first and second ultra low pressure plenums can be low profile. In one embodiment, the system including the first and second ultra low pressure plenums can be positioned underneath the sheets of a bed, such as a hospital bed. Alternatively, the system including the first and second ultra low pressure plenums can be placed above the sheets for aiding in patient turning and repositioning.

Gripping handles can be provided on either edge of the first ultra low pressure plenum to aid in movement of the first ultra low pressure plenum when a patient supported by the first ultra low pressure plenum. In this embodiment, the gripping handles can be placed over the sheet and unweighted to allow the patient to be moved for turning and repositioning of the patient. In one embodiment, the gripping handles are holes in the cover. In an alternative embodiment, the gripping handles are placed under the sheet and have a high coefficient of friction to prevent movement of the ultra low pressure plenum.

The inner positioner includes a bladder preferably filled with a fluidized particulate material with sufficient size and shape to micro-contour to a received body part, such as, but not limited to, bony prominences of which contact a surface when the body is positioned in a prone position and when the body is turned to other positions. The surface area of the inner positioner provides greater positive air displacement in the outer support plenum than would occur from the body part of the patient by itself. In one embodiment, the inner positioner can have a greater width than the patient. The inner positioner provides three dimensional movement. The positioner can displace and contour three dimensionally as though it was fluid while not having flow characteristics that would result in migration of the medium under the force of gravity. The positioner can provide three dimensional contouring. The positioner can be shaped as a pad.

In an alternate embodiment, the system provides a support including an outer support plenum providing a gross contouring and an inner positioner providing micro contouring. The outer support plenum can include a fluidized medium such as for example expanded foam beads contained therein. A lubricant can be used on the outside of the beads or in the interstitial spaces between the beads. Alternatively, kinetic sand can be retained in the outer support plenum. The outer support plenum can retain its shape after molding to a received body part. In one embodiment, a valve coupled to the outer support plenum can be used to pump air into the outer support plenum or draw down vacuum within the outer support plenum. The outer support plenum provides support for proper body alignment and keeping a received body part in position.

In one embodiment, the inner positioner is first molded around a received body part to provide micro-contouring. After molding of the inner positioner, the outer support plenum can be molded around the inner positioner to provide macro-contouring and retaining of the inner positioner in place. The fluidized medium in the inner positioner closest to the skin can be the more flowable than the fluidized in the outer support plenum to prevent friction, shear and interface pressure on capillaries of received body parts and prevent nerve entrapment.

The invention will be more fully described by reference to the following drawings.

BRIEF DESCRIPTION OF THE DRAWINGS

FIGS. 1A-1C are a schematic diagrams of a first bladder used in a system for body support in accordance with the teachings of the present invention.

DETAILED DESCRIPTION

Figure 1B:
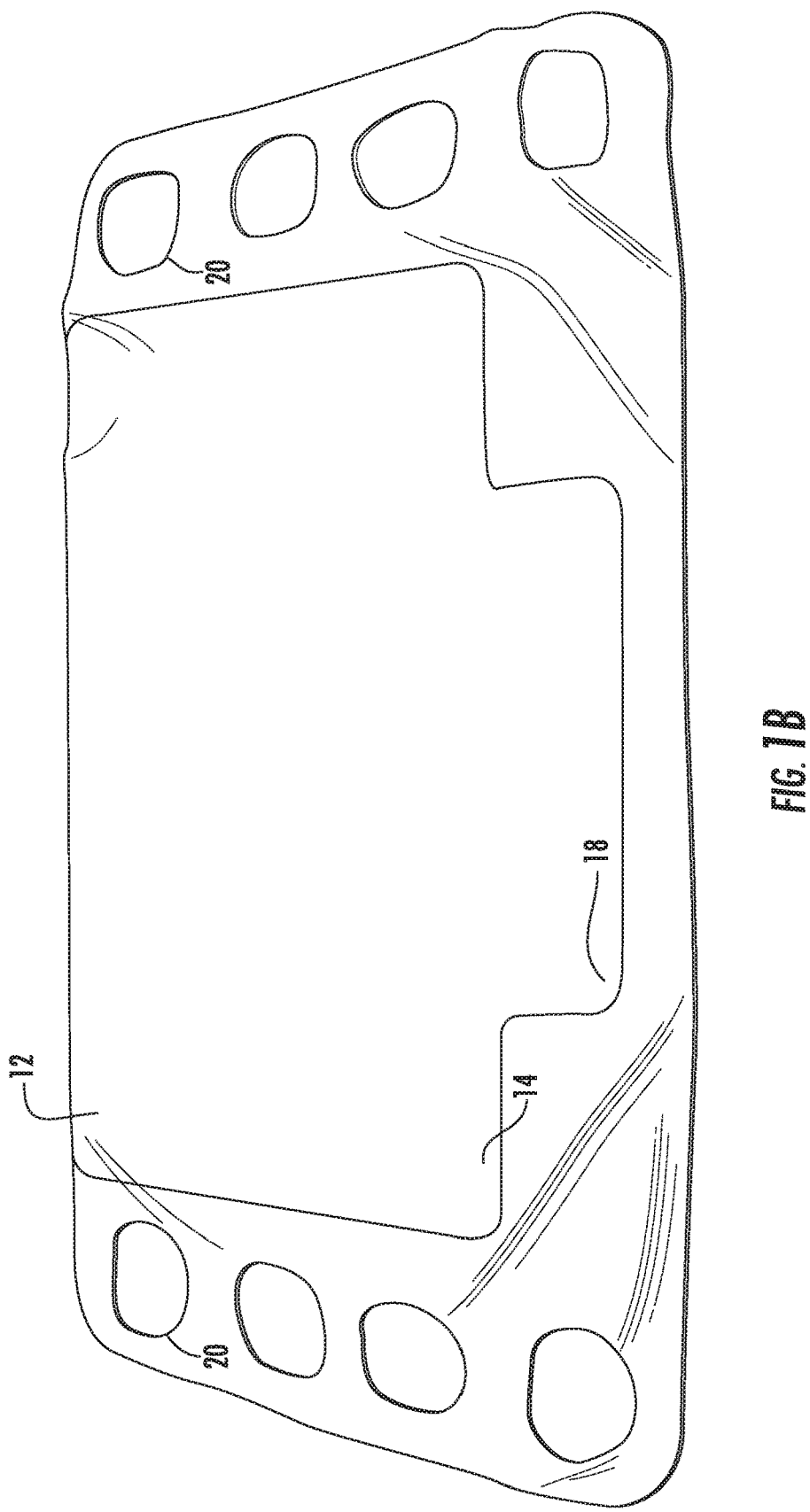

Reference will now be made in greater detail to a preferred embodiment of the invention, an example of which is illustrated in the accompanying drawings. Wherever possible, the same reference numerals will be used throughout the drawings and the description to refer to the same or like parts.

FIGS. 1-4 illustrate system for support of a body part of a patient turning and repositioning of the patient with simultaneous offloading of the bony prominences 10 in accordance with the teachings of the present invention. First ultra low pressure plenum 12 is configured to a shape to fit underneath a patient and support the lower back and/or hips of a patient. For example, first ultra low pressure plenum 12 can have a width $W_1$ of approximately 52 inches, and a height $H_1$ of about 35 inches. Alternatively, width $W_1$ can be a width of a bed, such as a hospital bed. First ultra low pressure plenum 12 is formed of upper bladder 14 and lower bladder 16. First upper bladder 14 can have a width $W_2$ and height $H_2$. Lower bladder 16 has a smaller width dimension $W_3$ and height dimension $H_3$ than upper bladder 14. Air pressure within upper bladder 14 and lower bladder 16 is reduced sufficiently for distributing pressure within first ultra low pressure plenum 12, but is not providing support of the received body part by itself. Upper bladder section 14 extends between edges 13a-13d. Lower bladder section 16 extends between edges 15a-15d.

Gripping handles 20 can be provided on either edge 22a, 22b to aid in movement of first ultra low pressure plenum 12 over surface 19. Gripping handles 20 can be placed over a sheet of a bed and unweighted to allow the patient to be moved. In an alternative embodiment, gripping handles 20 are placed under the sheet and have a high coefficient of friction to prevent movement of first ultra low pressure plenum 12.

Figure 2:
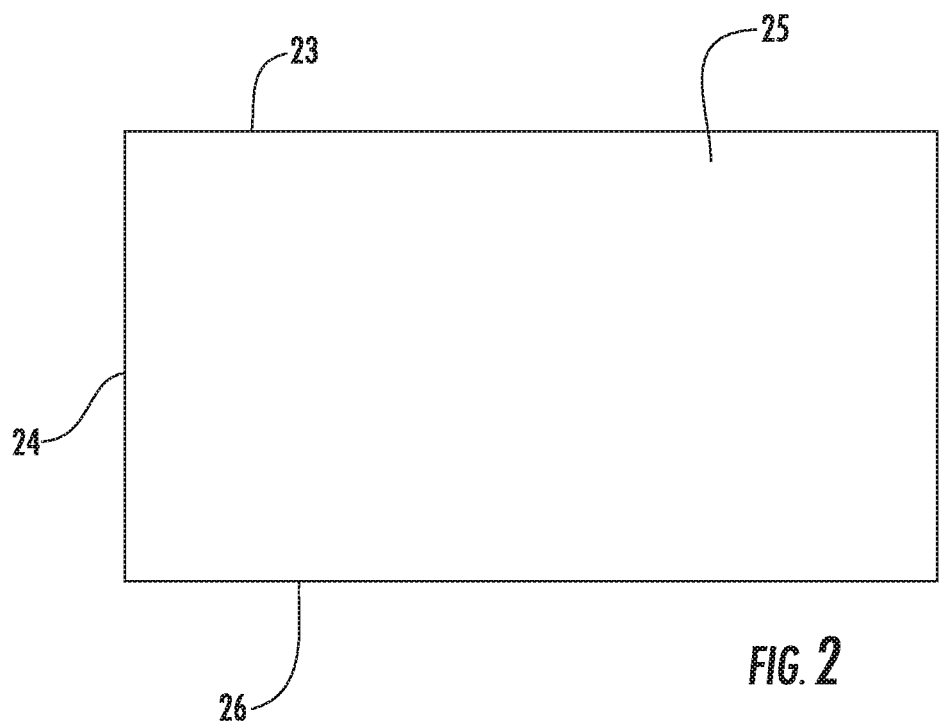
FIG. 2 is a schematic diagram of a positioner used in the system.

Positioner 23 can include bladder 24, as shown in FIG. 2. Bladder 24 is filled with fluidized material 25 which can retain its shape after sculpting. The flowability or lubricity of fluidized material 25 can be increased by adding a lubricant or by the removal of air from the interstitial spaces or both. The preferred medium of fluidized material 25 is a particulate material that has been modified in such a way that it acts like a fluid. Fluidized material 25 refers to a compound or composition which can be sculpted and retain its shape and has no memory or substantially no memory. The no memory or substantially no memory feature enables bladder 24 to increase in height and maintain support of a body part. Fluidized material 25 is made of a viscosity that will allow it to contour but not collapse under the weight of the body part.

At sea level, the normal interstitial air pressure would exceed about 760 millibars of mercury. This increases or decreases marginally as altitude varies. Depending on the nature of the particulate fluidized material 25, the pressure can be lowered below about 500 millibars to about 5 millibars, preferably, 350 millibars to about 5 millibars, while still maintaining the necessary flow characteristics of the product.

Fluidized material 25 can include compressible and non-compressible beads, such as polyethylene or polystyrene (PS) beads, expanded polyethylene (PE), crosslinked expanded polyethylene (PE), polypropylene (PP) pellets, closed cell foams, microspheres, encapsulated phase changing materials (PCM). The beads can be hard shelled or flexible. In one embodiment, the beads are flexible and air can be evacuated from the beads. In one embodiment, hard beads can be mixed with flexible beads in which air can be evacuated from the flexible beads. In an alternative embodiment, fluidized material 25 can a porous foam substance including pockets of interstitial air. In one embodiment, fluidized material 25 can be a polyurethane foam. The polyurethane foam can be open or closed cell and cut into small shapes such as spheres or blocks. For example, a sphere of polyurethane foam can have a size of 2 inches in diameter. For example, a block of polyurethane foam can be a 1×1×1 inch block.

Suitable examples of fluidized material 25 can be formed of a mixture of microspheres and lubricant. The microspheres can include hollow or gas-filled structural bubbles (typically of glass or plastic) with an average diameter of less than 200 microns. The composition flows and stresses in response to a deforming pressure exerted on it and the composition ceases to flow and stress when the deforming pressure is terminated. For example, fluidized material 25 can be formed of a product referred to as Floam™. A flowable compound comprising lubricated microspheres, including the compound itself, formulations for making the compound, methods for making the compound, products made from the compound and methods for making products from the compound as defined by U.S. Pat. Nos. 5,421,874, 5,549,743, 5,626,657, 6,020,055, 6,197,099 and 8,175,585, each of which is hereby incorporated by reference into this application.

For example, bladder 24 can be formed of a flexible plastic, such as urethane. Upon removal of gas from fluidized material 25, bladder 24 flows concurrent with the flow of fluidized material 25 such that bladder 24 moves with movement of fluidized material 25. For example, the gas can be air, helium, hydrogen or nitrogen. Optionally, gas can communicate throughout the whole bladder for allowing maximum contouring and functional displacement of both the gas and the fluidized chamber thereby providing maximum contouring to a desired body part.

Figure 3:
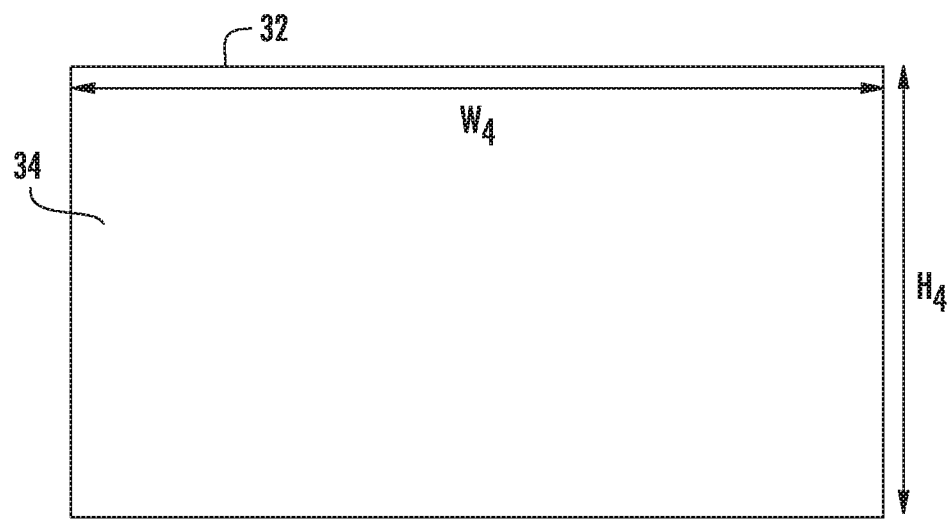
FIG. 3 is a schematic diagram of a second bladder used in the system.

FIG. 3 is a schematic diagram of second ultra low pressure plenum 32. Second ultra low pressure plenum 32 is formed of bladder 34. Second ultra low pressure plenum 32 can have a width $W_4$ and a height $H_4$ that is identical or substantially similar to height $H_2$ and width $W_2$ of upper bladder 14 of the first ultra low pressure plenum 12.

Figure 4:
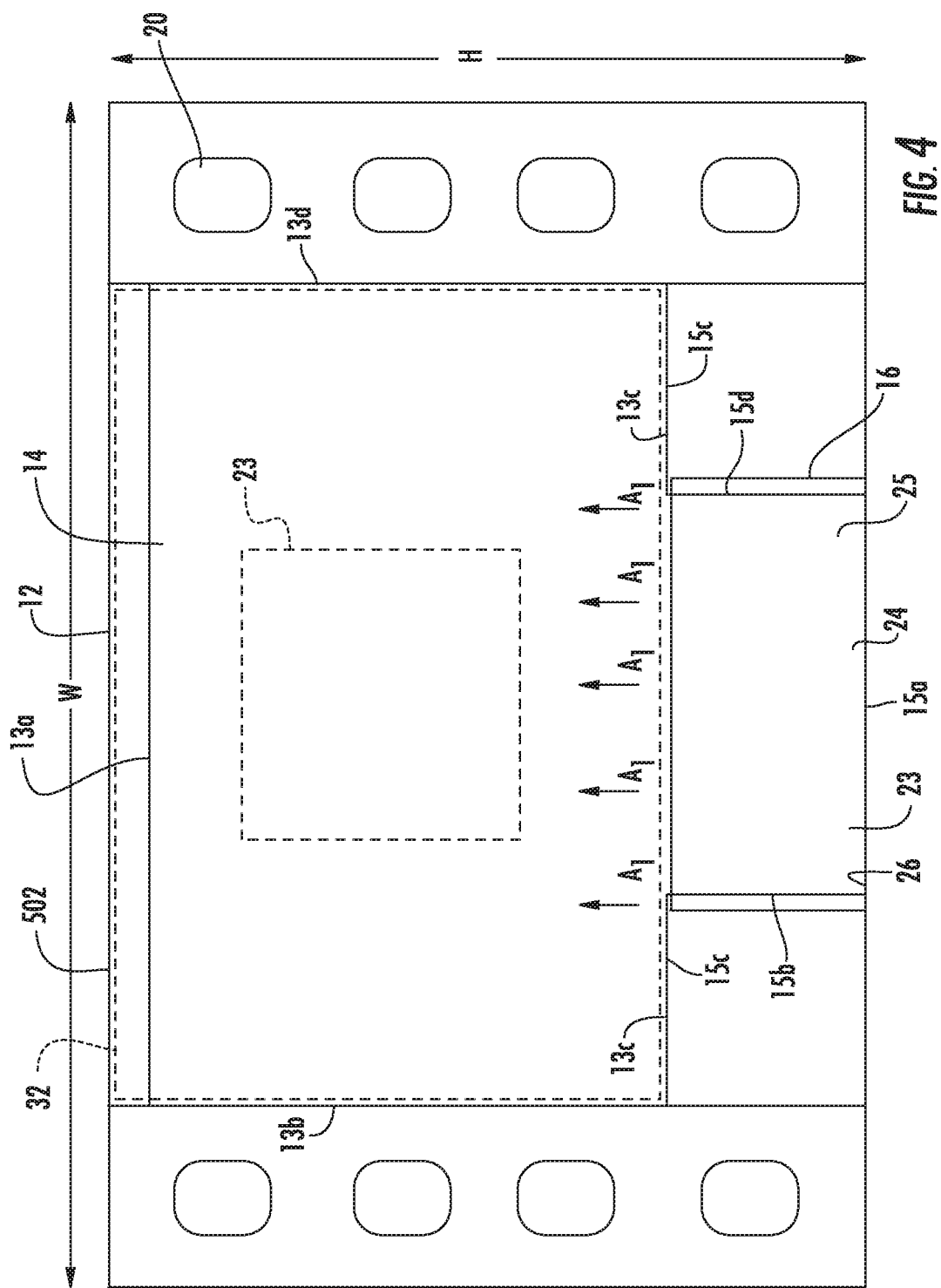
FIG. 4 is a schematic diagram of the system including the first and second bladders and the positioner.

Second ultra low pressure plenum 32 can be placed under first ultra low pressure plenum 12 as shown in FIG. 4. Alternatively, the second ultra low pressure plenum can be placed on top of the first ultra low pressure plenum. Positioner 23 is placed beneath both the first ultra low pressure plenum 12 and second ultra low pressure plenum 32. Positioner 23 displaces air in both the first ultra low pressure plenum 12 and second ultra low pressure plenum 32. Lower surface 26 of positioner 23 can be formed of a high friction material for preventing movement of positioner 23.

Bladder 24 is preferably filled with fluidized particulate material 25 with sufficient size and shape to displace an amount of gas in ultra low pressure plenum 12 and second ultra low pressure plenum 32 to offload pressure from the received body part, such as the bony prominences of the collar bone, rib cage and iliac crest when the body is in the prone position adjacent system 10. Bladder 24 provides micro-contouring because fluidized material 25 can respond three-dimensionally. Alternatively, bladder 24 is formed of any contouring medium, such as foam or gel which is sufficient to displace air within first ultra low pressure plenum 12 and second ultra low pressure plenum 32.

For example, the pressure in ultra low pressure plenum 12 and second ultra low pressure plenum 32 can be below 20 mm of water. It will be appreciated that all equivalents such as mm Hg and PSI can be used for measuring the pressure within ultra low pressure plenum 12 and second ultra low pressure plenum 32.

The pressure within ultra low pressure plenum 12 and second ultra low pressure plenum 32 can be below about 20 mm of water if no positioner 23 is used or if an area of less than about 30% of ultra low pressure plenum 12 and second ultra low pressure plenum 32 are covered by positioner 23. The pressure within ultra low pressure plenum 12 and second ultra low pressure plenum 32 can be below about 10 mm of water if an area of between about 30% to about 60% of ultra low pressure plenum 12 and second ultra low pressure plenum 32 is covered by positioner 23. The pressure within ultra low pressure plenum 12 and second ultra low pressure plenum 32 can be below about 5 mm of water if an area of greater than about 60% of ultra low pressure plenum 12 and second ultra low pressure plenum 32 are covered by positioner 23.

Bottom surface 17 of first ultra low pressure plenum 12 or second ultra low pressure plenum 32 can be formed of a material having a low coefficient of friction to be used to move a patient on surface 19 underneath first ultra low pressure plenum 12 or second ultra low pressure plenum 32. A suitable material having a low coefficient of friction is nylon or rip stop nylon material. Upper surface 18 of first ultra low pressure plenum 12 or second ultra low pressure plenum 32 can be formed of a material having a high coefficient of friction. A suitable material having a high coefficient of friction is a rubberized or non-skid material.

An additional positioner 23 can be placed over lower bladder 16 of ultra low pressure plenum 12 to displace gas from lower bladder 16 to upper bladder 14 in the direction of arrows A₁, as shown in FIG. 4 or at various locations on first ultra low pressure plenum 12 or second ultra low pressure plenum 32. When a patient is recumbent on first ultra low pressure plenum 12 and second ultra low pressure plenum 32, gas will be displaced in upper bladder 14 and second ultra low pressure plenum 32, towards outer edges 13a for providing support adjacent to edges 13b and 13d thereby providing support of edges 13b and 13d of upper bladder 14 of the patient within edges 13b and 13d and to the edges of bladder 34 for lifting a patient from surface 11.

Figure 5:
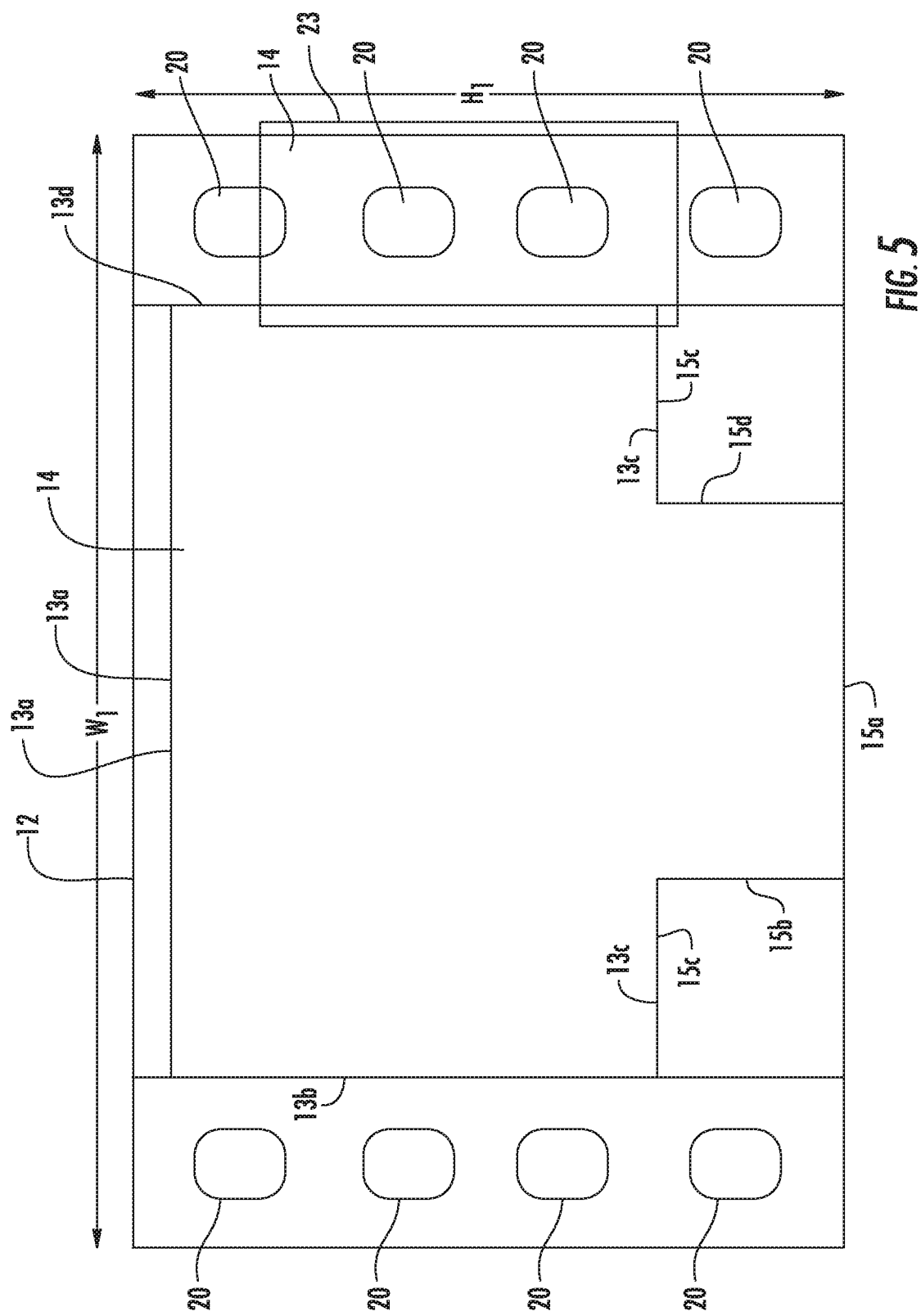
FIG. 5 is a schematic diagram of the system including the positioner positioned at an outer wall of the support.

In one embodiment, positioner 23 can be positioned at one of edges 13b and 13d to push air away from respective edges 13b and 13d thereby aiding in turning of a patient towards the opposite edge, as shown in FIG. 5. For example, if the patient is to be turned towards edge 13d, positioner 23 can be placed at edge 13b for displacing gas behind the patient to towards edge 13b of upper bladder 14, thereby pneumatically assisting in turning of the patient to face edge 13d.

System 10 including ultra low pressure plenum 12 and second ultra low pressure plenum 32 is functional whether positioner 23 is placed on top of ultra low pressure plenum 12 and second ultra low pressure plenum 32 or beneath ultra low pressure plenum 12 and second ultra low pressure plenum 32.

Figure 6:
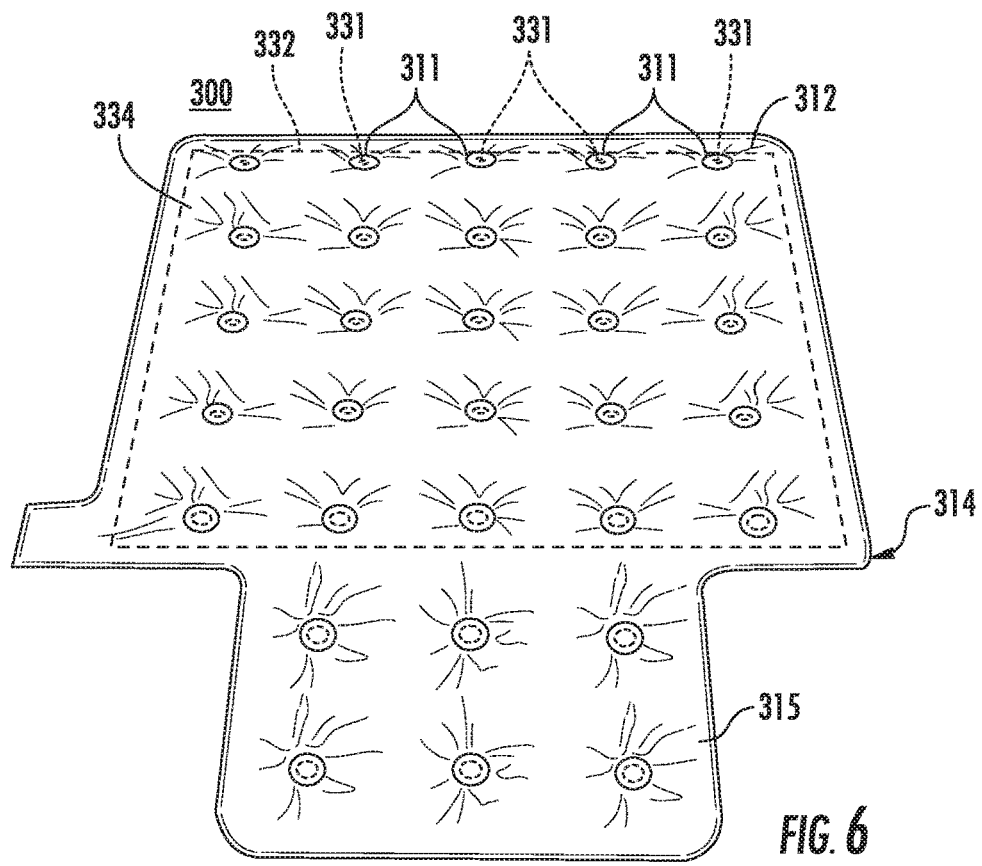
FIG. 6 is a schematic diagram of an alternate embodiment of a system for support of a body part in accordance with the teachings of the present invention which provides low pressure loss.

FIGS. 6-17 illustrate system for support of a body part of a patient turning and repositioning of the patient with simultaneous offloading of the bony prominences 300 in accordance with the teachings of the present invention. System 300 includes first ultra low pressure plenum 312 and second low pressure plenum 332, as shown in FIG. 6. First ultra low pressure plenum 312 is configured to a shape to fit underneath a patient and support the lower back and/or hips of a patient. First ultra low pressure plenum 312 can include upper bladder 314 and extension bladder 315. Extension bladder 315 extends from upper bladder 314. Extension bladder 315 and upper bladder 314 can be integral to one another. Air pressure within upper bladder 314 and extension bladder 315 is reduced sufficiently for distributing pressure within first ultra low pressure plenum 312, but is not providing support of the received body part by itself. Second ultra low pressure plenum 332 is formed of bladder 334. Second ultra low pressure plenum 32 can be placed under first ultra low pressure plenum 12. Dimples 311 can be formed in first ultra low pressure plenum 312 and dimples 331 can be formed in second ultra low pressure plenum 332. Dimples 311 and dimples 331 can be aligned with one another.

Figure 7:
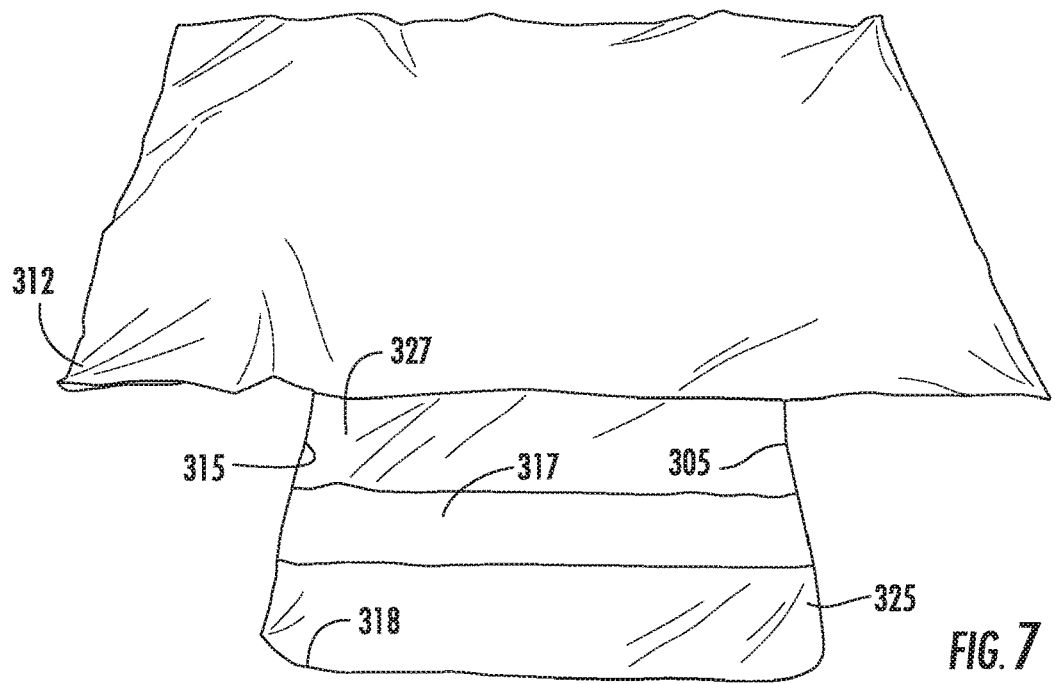
FIG. 7 is a front view of a cover placed over the support shown in FIG. 6.
Figure 8:
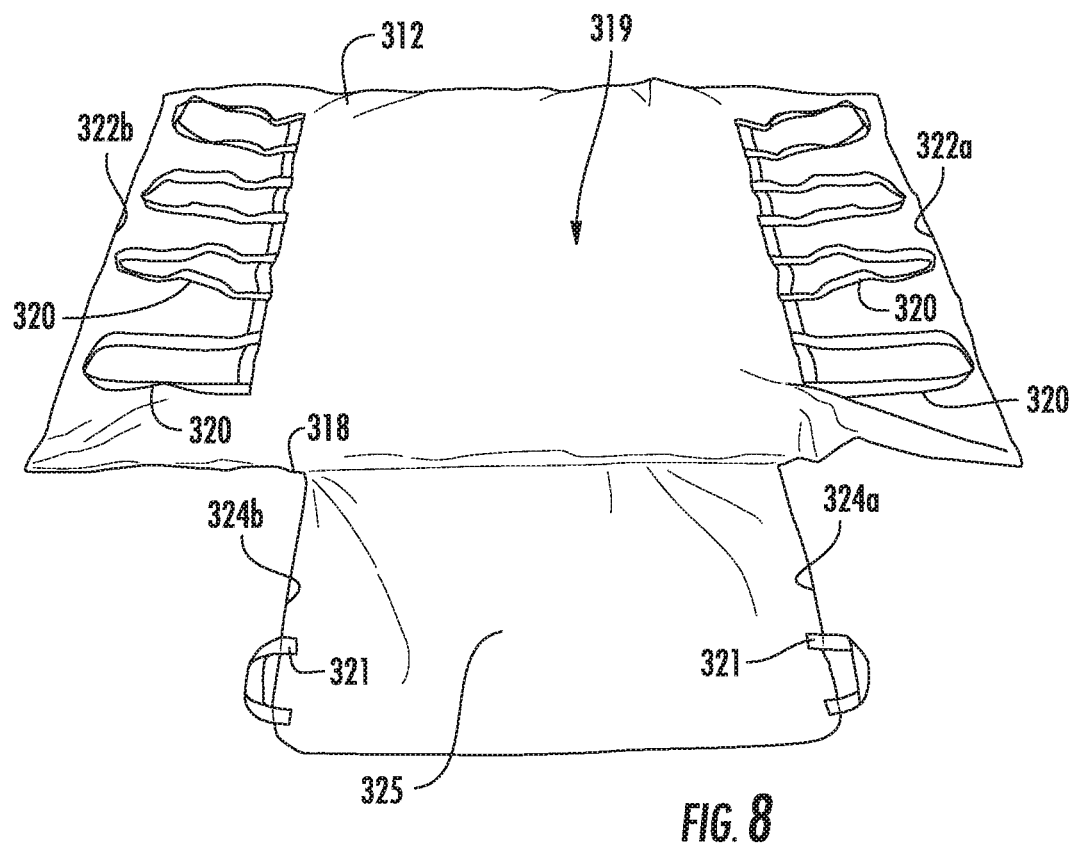
FIG. 8 is a rear view of a cover placed over the support shown in FIG. 6.
Figure 9:
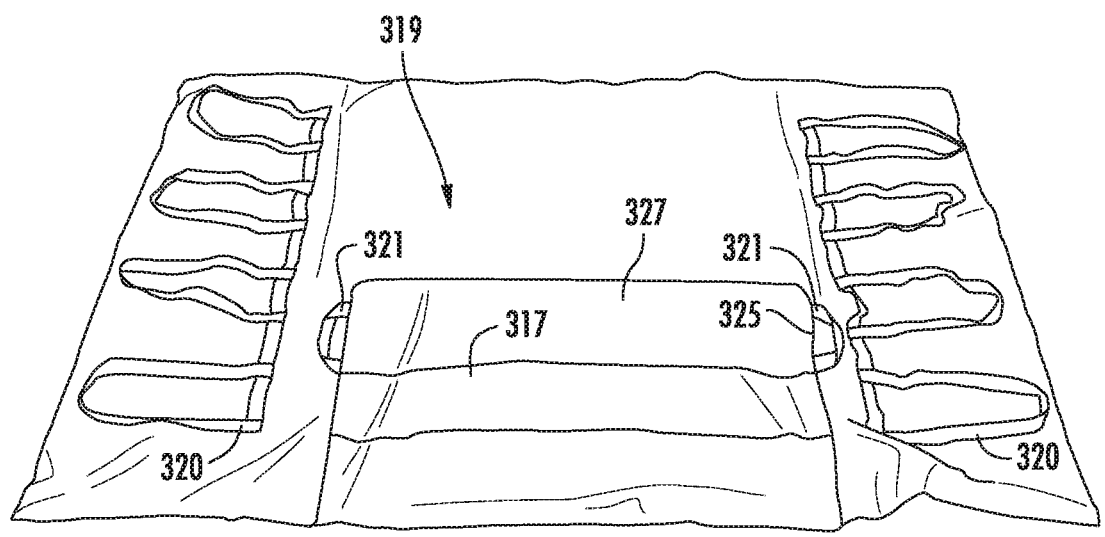
FIG. 9 is a rear view of a cover placed over the support shown in FIG. 6 including an extension of the support placed in a folded condition.

Cover 318 can be placed around first ultra low pressure plenum 312 and second ultra low pressure plenum, as shown in FIGS. 7-9. Cover 318 can be formed of a material having a low coefficient of friction. A suitable material having a low coefficient of friction is nylon or rip stop nylon material. Extension 325 of cover 318 receives extension bladder 315.

Portion 317 on upper surface 327 of extension 325 can be formed of a material having a high coefficient of friction. A suitable material having a high coefficient of friction is a rubberized or non-skid material. Portion 317 can be folded underneath rear surface 319 of upper bladder 314 to prevent movement of ultra low pressure plenum 312, as shown in FIG. 9. Handles 320 can be provided adjacent either edge 322a, 322b of cover 318 to aid in movement. Handles 321 can be provided adjacent either edge 324a, 324b of extension 325 of cover 318 to aid in folding of extension 325 underneath rear surface 319.

Figure 10:
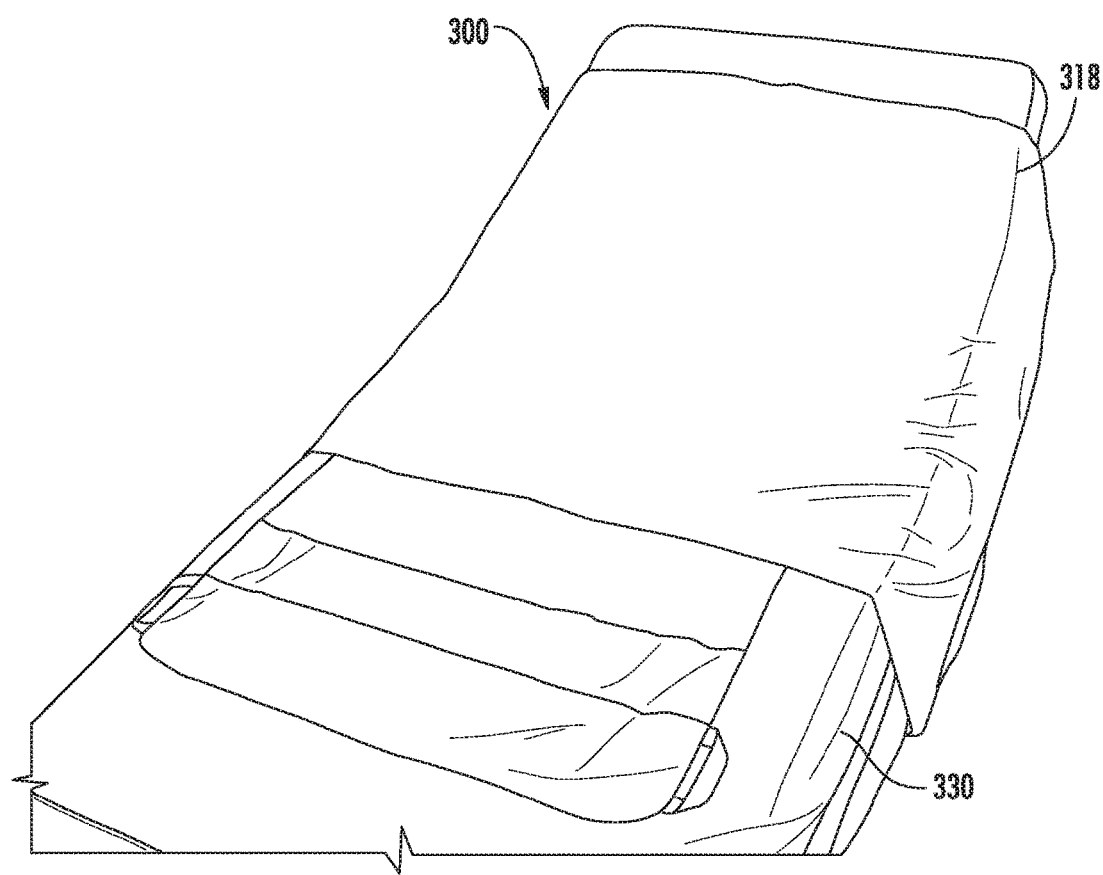
FIG. 10 is a schematic diagram of the system in accordance with the teachings of the present invention when placed on a bed.
Figure 11:
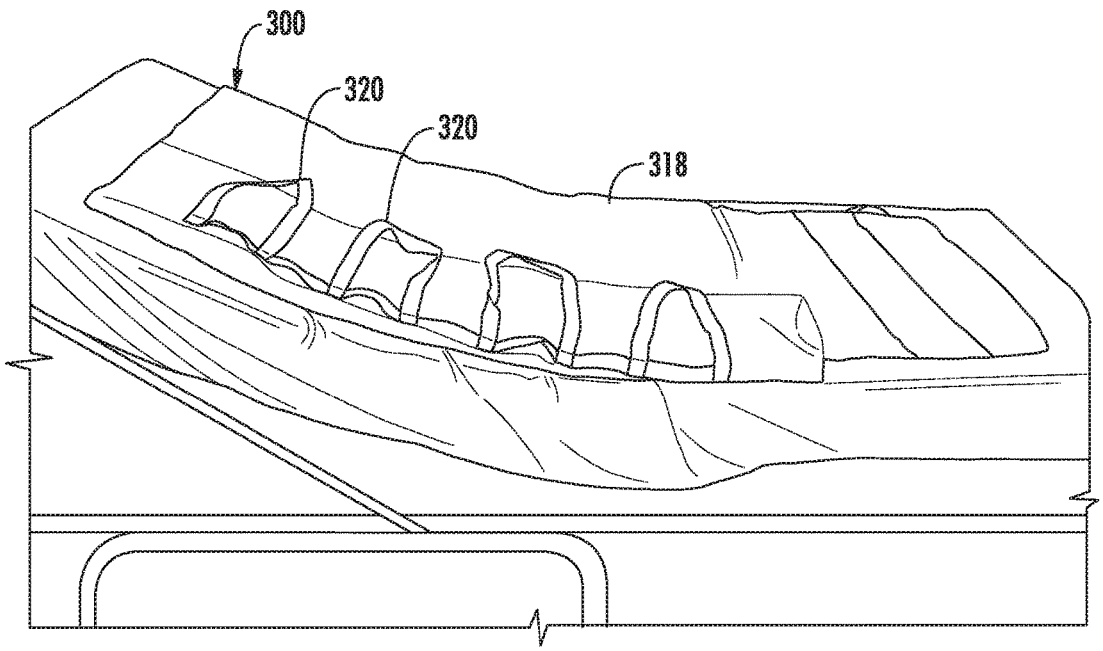
FIG. 11 is a schematic diagram of the system in accordance with the teachings of the present invention when placed on a bed and having one side folded to expose handles attached to a rear side of the support.

FIGS. 10-17 illustrate use of system for support of a body part of a user turning and repositioning of the user with simultaneous offloading of the bony prominences 300. In FIG. 10, system for support of a body part of a user turning and repositioning of the user with simultaneous offloading of the bony prominences 300 can be placed on bed 330. System 300 can be moved to different positions on bed 330 using handles 320, as shown in FIG. 11.

Figure 12:
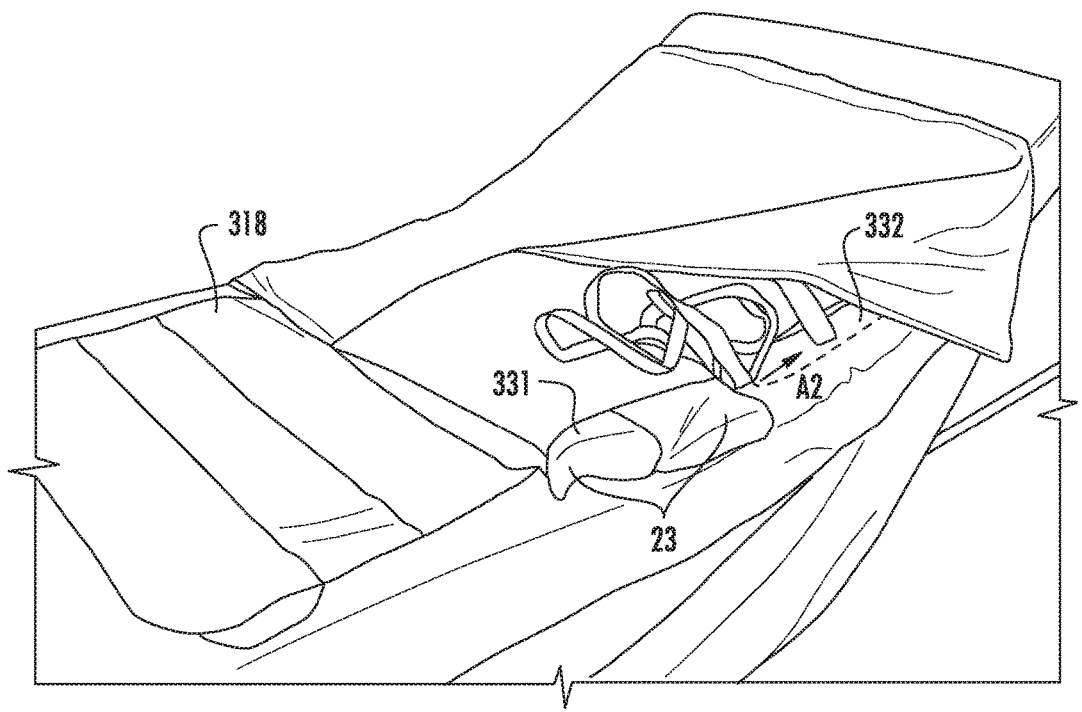
FIG. 12 is a schematic diagram of the system in accordance with the teachings of the present invention when placed on a bed and including a positioner placed in a retainer of the cover.
Figure 13:
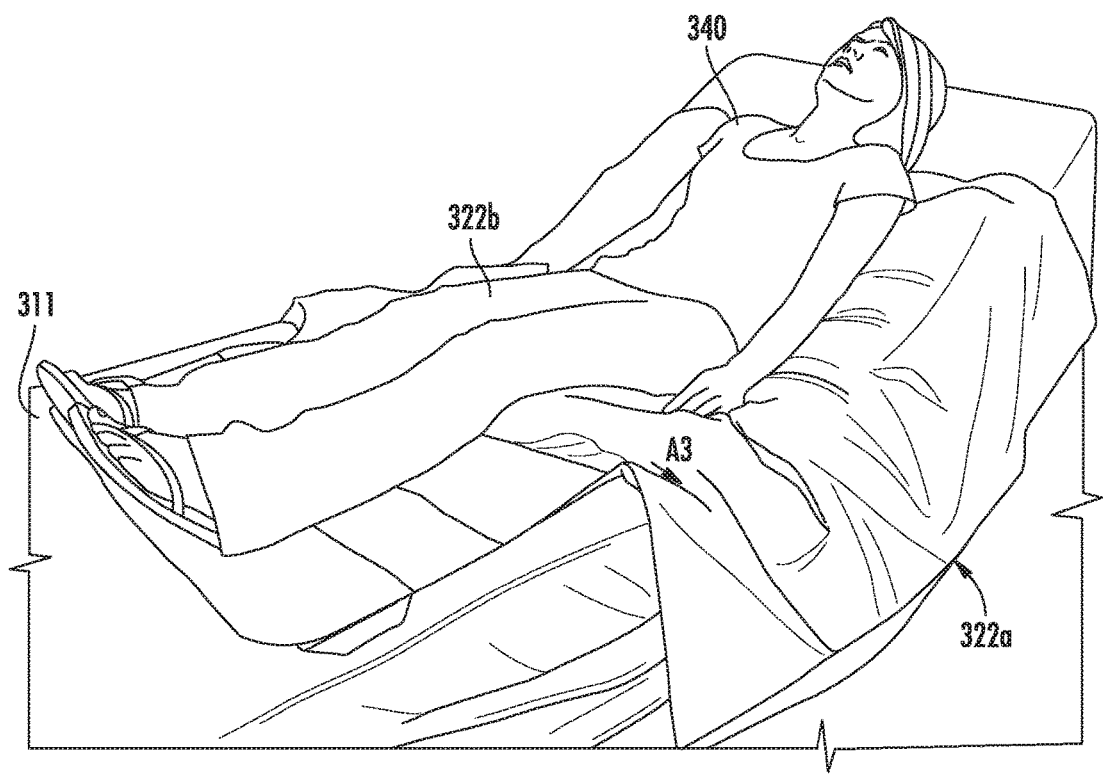
FIG. 13 is a schematic diagram of the system in accordance with the teachings of the present invention when placed on a bed and in use by a user.
Figure 14:
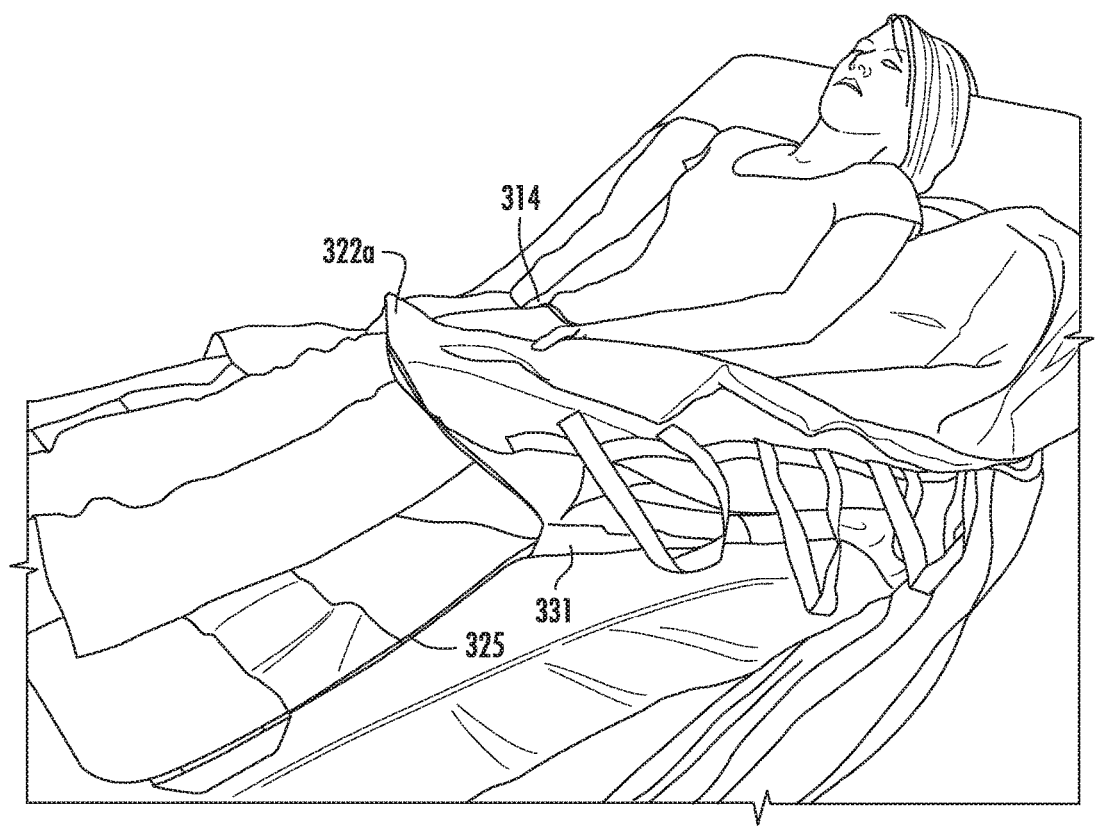
FIG. 14 is a schematic diagram of the system in accordance with the teachings of the present invention when placed on a bed and in use by a user during folding of an edge towards the user.
Figure 15:
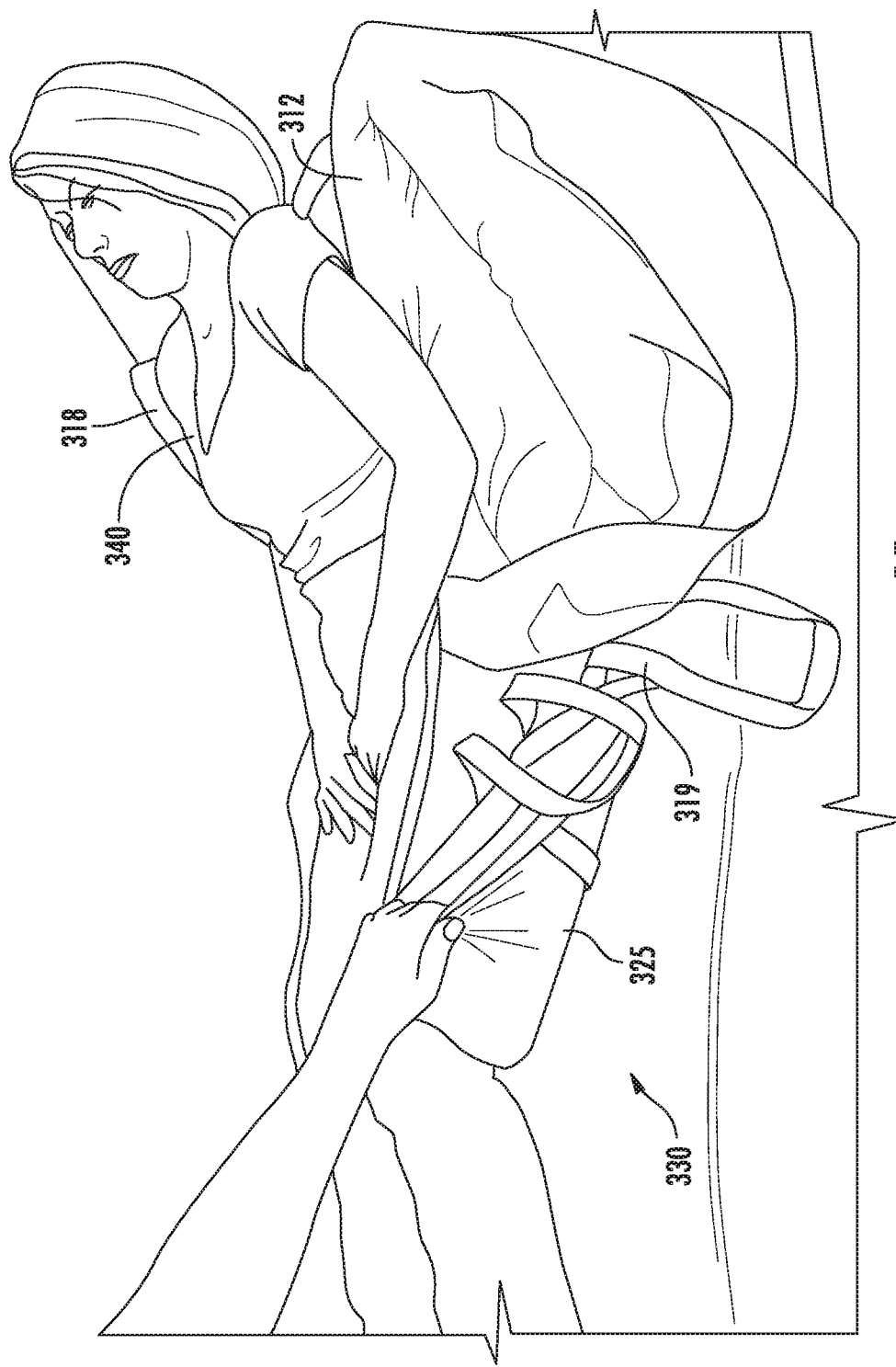
FIG. 15 is a schematic diagram of the system in accordance with the teachings of the present invention when placed on a bed and in use by a user during folding of an extension of the cover and support.

Positioner 23 can be placed within pocket 331 of cover 318 to retain positioner 23. Positioner 23 can be placed over upper bladder 314 of first ultra low pressure plenum 312 to displace gas in the direction of arrow A₂, as shown in FIG. 12. When a user is recumbent on first ultra low pressure plenum 312 with their sacrum received on positioner 23, gas will be displaced in upper bladder 314 in the direction of arrow A₃ towards outer edges 322a, 322b for providing support adjacent to edges 322a and 322b thereby providing support of the user within edges 322a and 322b and lifting user 340 from surface 311 of bed 330 and offloading the sacrum and trochanter of user 340, as shown in FIG. 13 and allow the body to be rotated over the support or bed. Additional positioners 23 can be placed in pocket 331 of cover 118 by lifting edge 322a to provide additional displacement of gas within upper bladder 314 as shown in FIG. 14. Extension 325 can be folded underneath rear surface 319 of upper bladder 314 to prevent movement of ultra low pressure plenum 312, as shown in FIG. 15.

Figure 16:
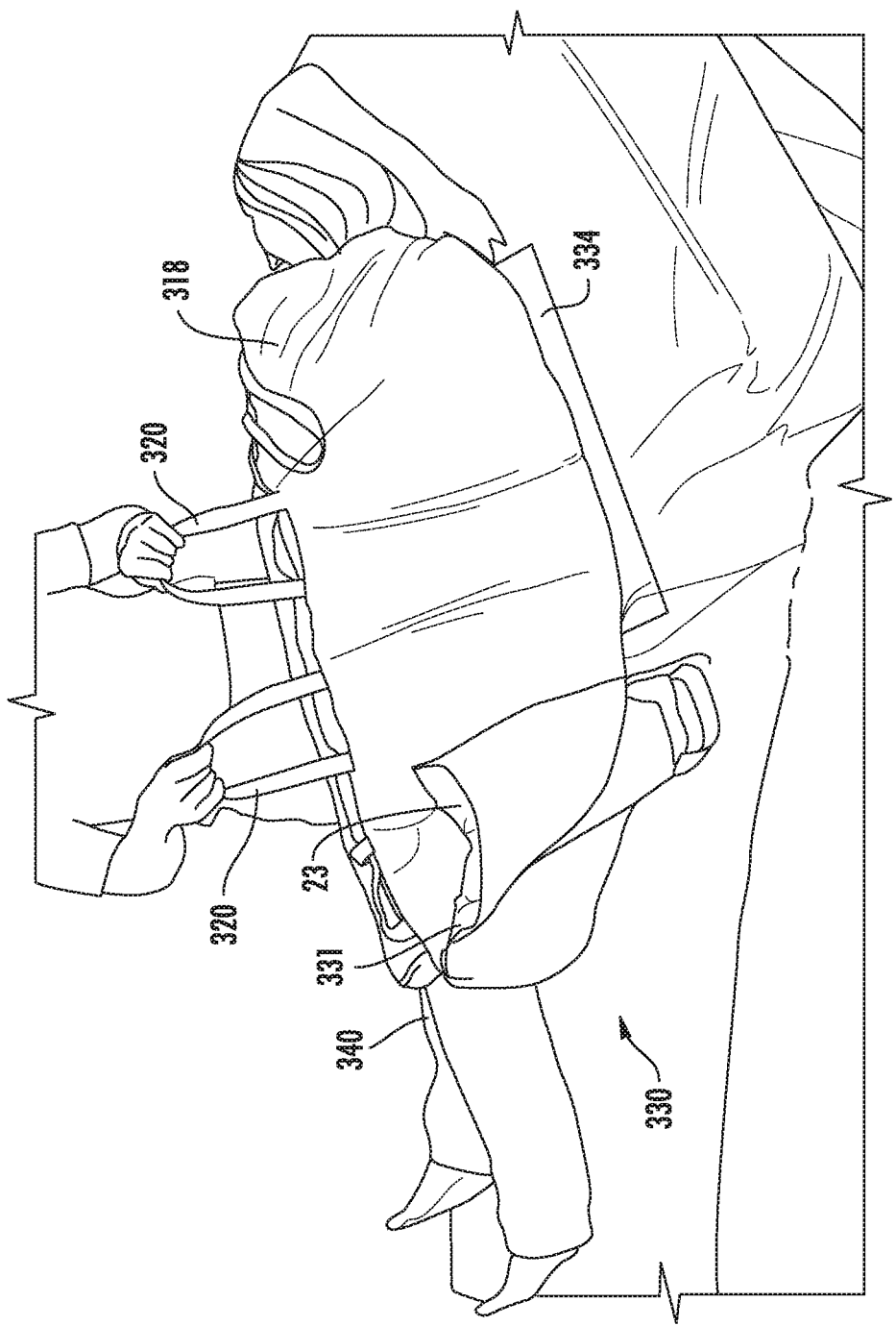
FIG. 16 is a schematic diagram of the system in accordance with the teachings of the present invention when placed on a bed and in use by a user during turning of the user.
Figure 17:
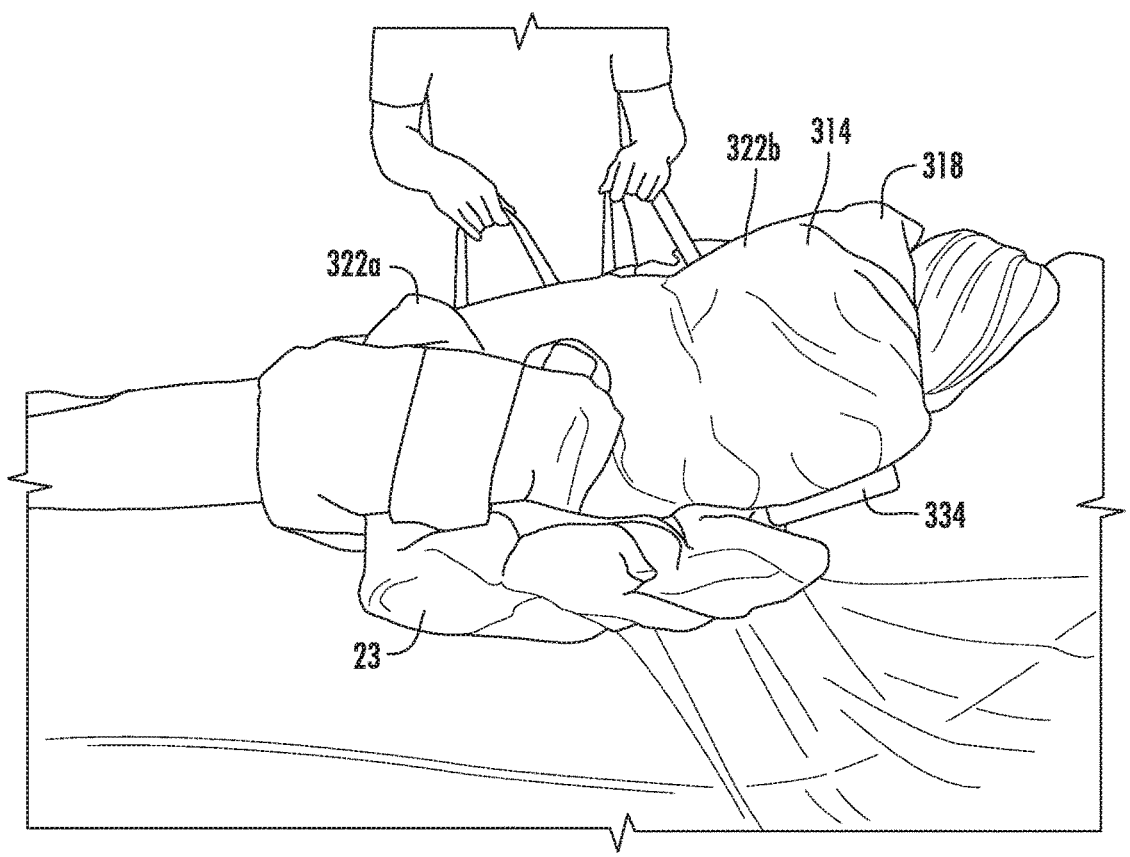
FIG. 17 is a schematic diagram of the system in accordance with the teachings of the present invention when placed on a bed and in use including use of a positioner to aid in turning.

In one embodiment, user 340 can be moved or turned by using handles 320, as shown in FIG. 16. In one embodiment, positioner 23 can be positioned behind a side of cover 318 to push gas away from edges 322a, thereby aiding in turning of a user towards the opposite edge, as shown in FIG. 17. For example, if the patient is to be turned towards edge 322b, positioner 23 can be placed at edge 322a for displacing gas behind the patient to towards edge 322b of upper bladder 314, thereby pneumatically assisting in turning of the patient to face edge 322b.

Figure 18:
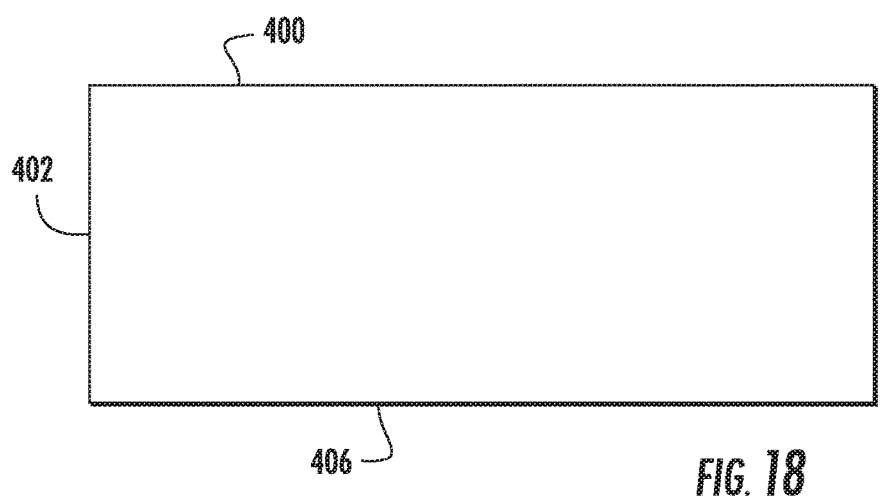
FIG. 18 is a schematic diagram of an alternate embodiment of a positioner used in the system.

In one embodiment, positioner 400 can include ultra low pressure bladder 402, as shown in FIG. 18. The pressure within ultra low pressure bladder 402 is a range of less than about 20 mm of water to about 5 mm of water or a range of less than about 10 mm of water to about 5 mm of water. It will be appreciated that all equivalents such as mm Hg and PSI can be used for measuring the pressure within ultra low pressure bladder 402. In this embodiment, positioner 400 is formed with sufficient size and shape to displace an amount of gas in ultra low pressure bladder 402 to offload pressure from the received body part. Lower surface 406 of positioner 400 can be formed of a high friction material for preventing movement of positioner 400. Positioner 400 can be placed on top of first ultra low pressure plenum 12 and/or or second ultra low pressure plenum 32 or beneath ultra low pressure plenum 12 and/or second ultra low pressure plenum 32.

Positioner 400 can be placed over lower bladder 16 of ultra low pressure plenum 12 to displace gas from lower bladder 16 to upper bladder 14 in the direction of arrows A₁, as shown in FIG. 4.

In one embodiment, positioner 23 can be used together with positioner 400. Positioner 400 can be placed over lower bladder 16 of ultra low pressure plenum 12 positioner 23 can be positioned at one of edges 13b and 13d to push air away from respective edges 13b and 13d thereby aiding in turning of a patient towards the opposite edge, similar to positioner 23 as shown in FIG. 5. For example, if the patient is to be turned towards edge 13d, positioner 23 can be placed at edge 13b for displacing gas behind the patient to towards edge 13b of upper bladder 14, thereby pneumatically assisting in turning of the patient to face edge 13d.

Figure 19:
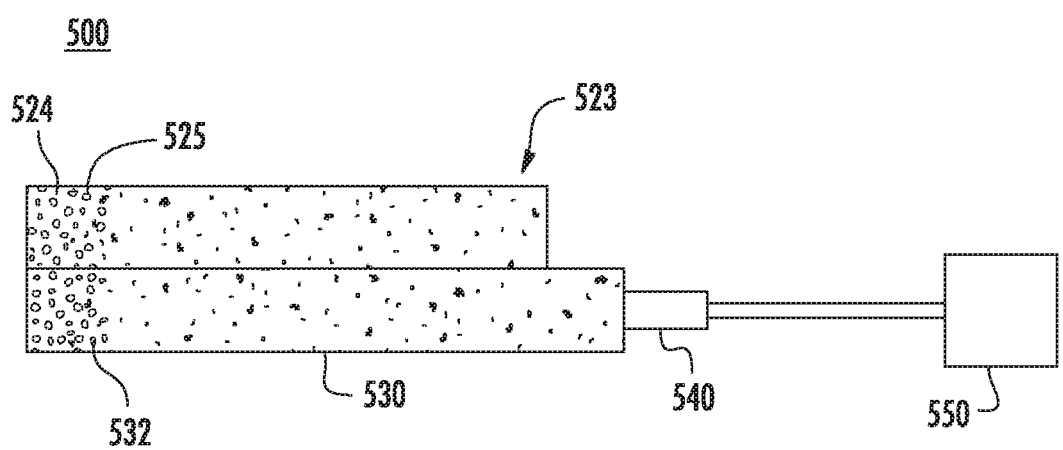
FIG. 19 is a schematic diagram of an alternate embodiment of a system for body support.

FIG. 19 is an alternate embodiment of system for support of a body part of a patient turning and repositioning of the patient with simultaneous offloading of the bony prominences 500. Positioner 523 can include inner bladder 524. Inner bladder 524 is filled with fluidized material 525 which can retain its shape after sculpting. The flowability or lubricity of fluidized material 525 can be increased by adding a lubricant or by the removal of air from the interstitial spaces or both. The preferred medium of fluidized material 525 is a particulate material that has been modified in such a way that it acts like a fluid. Fluidized material 525 refers to a compound or composition which can be sculpted and retain its shape and has no memory or substantially no memory. The no memory or substantially no memory feature enables bladder 524 to increase in height and maintain support of a body part. Fluidized material 525 is made of a viscosity that will allow it to contour but not collapse under the weight of the body part.

At sea level, the normal interstitial air pressure would exceed about 760 millibars of mercury. This increases or decreases marginally as altitude varies. Depending on the nature of the particulate fluidized material 525, the pressure can be lowered below about 500 millibars to about 5 millibars, preferably, 350 millibars to about 5 millibars, while still maintaining the necessary flow characteristics of the product.

Fluidized material 525 can include compressible and non-compressible beads, such as polyethylene or polystyrene (PS) beads, expanded polyethylene (PE), crosslinked expanded polyethylene (PE), polypropylene (PP) pellets, closed cell foams, microspheres, encapsulated phase changing materials (PCM). The beads can be hard shelled or flexible. In one embodiment, the beads are flexible and air can be evacuated from the beads. In one embodiment, hard beads can be mixed with flexible beads in which air can be evacuated from the flexible beads. In an alternative embodiment, fluidized material 525 can a porous foam substance including pockets of interstitial air. In one embodiment, fluidized material 525 can be a polyurethane foam. The polyurethane foam can be open or closed cell and cut into small shapes such as spheres or blocks. For example, a sphere of polyurethane foam can have a size of 2 inches in diameter. For example, a block of polyurethane foam can be a 1×1×1 inch block.

Suitable examples of fluidized material 525 can be formed of a mixture of microspheres and lubricant. The microspheres can include hollow or gas-filled structural bubbles (typically of glass or plastic) with an average diameter of less than 200 microns. The composition flows and stresses in response to a deforming pressure exerted on it and the composition ceases to flow and stress when the deforming pressure is terminated. For example, fluidized material 525 can be formed of a product referred to as Floam™. A flowable compound comprising lubricated microspheres, including the compound itself, formulations for making the compound, methods for making the compound, products made from the compound and methods for making products from the compound as defined by U.S. Pat. Nos. 5,421,874, 5,549,743, 5,626,657, 6,020,055, 6,197,099 and 8,175,585, each of which is hereby incorporated by reference into this application.

Fluidized material 525 can be kinetic sand. Kinetic sand can mold three-dimensionally. Kinetic sand can be formed of 98% sand and 2% polydimethylsiloxane to mimic the physical properties of wet sand.

Fluidized material 525 can be a thixotropic fluid.

For example, bladder 524 can be formed of a flexible plastic, such as urethane. Upon removal of gas from fluidized material 525, bladder 524 flows concurrent with the flow of fluidized material 525 such that bladder 524 moves with movement of fluidized material 525. For example, the gas can be air, helium, hydrogen or nitrogen. Optionally, gas can communicate throughout the whole bladder for allowing maximum contouring and functional displacement of both the gas and the fluidized chamber thereby providing maximum contouring to a desired body part.

Outer bladder 530 is filled with fluidized material 532. Fluidized material 524 is a composition which has greater flow characteristics than fluidized material 532. Fluidized material 524 can be formed of a mixture of a lubricant and a material selected from the group comprising beads, polyethylene beads, polystyrene (PS) beads, expanded polyethylene (PE), crosslinked expanded polyethylene (PE), pellets, closed cell foams, microspheres, and encapsulated phase changing materials (PCM). Inner bladder 524 is adapted to be positioned adjacent a received body part to micro-contour to the received body part and outer bladder 530 macro-contours to inner bladder 524 after inner bladder 524 is micro-contoured to the received body part.

Valve 540 can be coupled to outer bladder 530. Valve 540 extending from outer bladder 530 permits the evacuation of all or some of the air from outer bladder 530 which causes outer bladder 530 to be reduced in size due to loss of air within fluidized material 524 and adjusts the rigidity of outer bladder 530. Pump 550 can be attached to valve 540 for pumping air or releasing air manually or automatically.

During operation, inner bladder 524 contacts a received body part to micro-contour to the body part. Outer bladder 14 is placed adjacent or underneath the inner bladder to macro-contour to inner bladder 524. In one embodiment, air is removed from outer bladder 530 with valve 540 to support inner bladder 524. After completion of use of system 500, valve 540 can be released thereby drawing air back into outer bladder 530.

Figure 20:
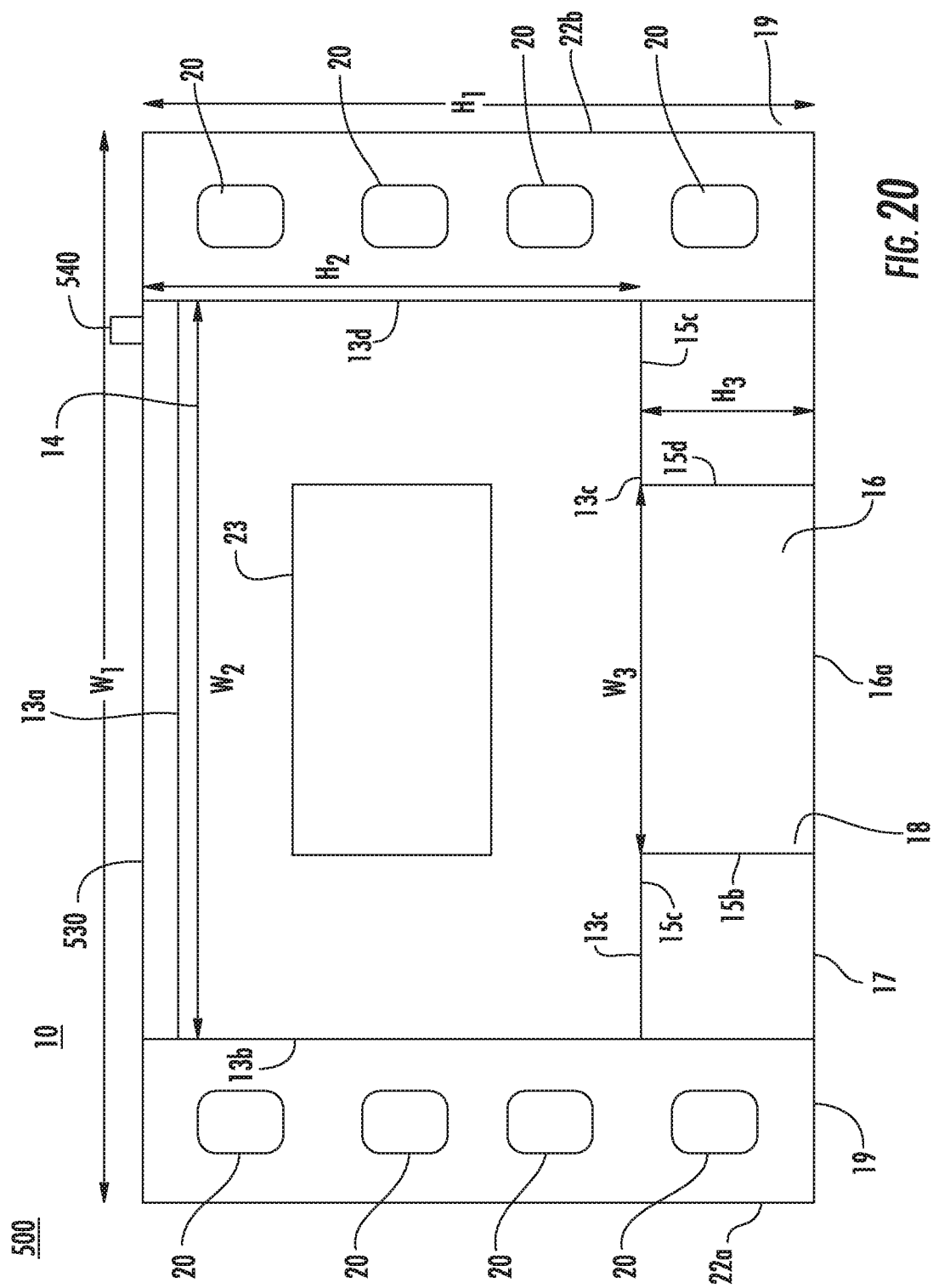
FIG. 20 is a schematic diagram of an outer bladder used in FIG. 18.

Outer bladder 530 can replace first ultra low pressure plenum 12 as shown in FIG. 20. Outer bladder 530 is configured to a shape to fit underneath a patient and support the lower back and/or hips of a patient. For example, outer bladder 530 can have a width $W_1$ of approximately 52 inches, and a height $H_1$ of about 35 inches. Alternatively, width $W_1$ can be a width of a bed, such as a hospital bed. Outer bladder 530 is formed of upper bladder 14 and lower bladder 16. First upper bladder 14 can have a width $W_2$ and height $H_2$. Lower bladder 16 has a smaller width dimension $W_3$ and height dimension $H_3$ than upper bladder 14. Air pressure within upper bladder 14 and lower bladder 16 is reduced sufficiently for distributing pressure within first ultra low pressure plenum 12, but is not providing support of the received body part by itself. Upper bladder section 14 extends between edges 13a-13d. Lower bladder section 16 extends between edges 15a-15d.

Gripping handles 20 can be provided on either edge 22a, 22b to aid in movement of outer bladder 530 over surface 19. Gripping handles 20 can be placed over a sheet of a bed and unweighted to allow the patient to be moved. In an alternative embodiment, gripping handles 20 are placed under the sheet and have a high coefficient of friction to prevent movement of outer bladder 530.

Figure 21:
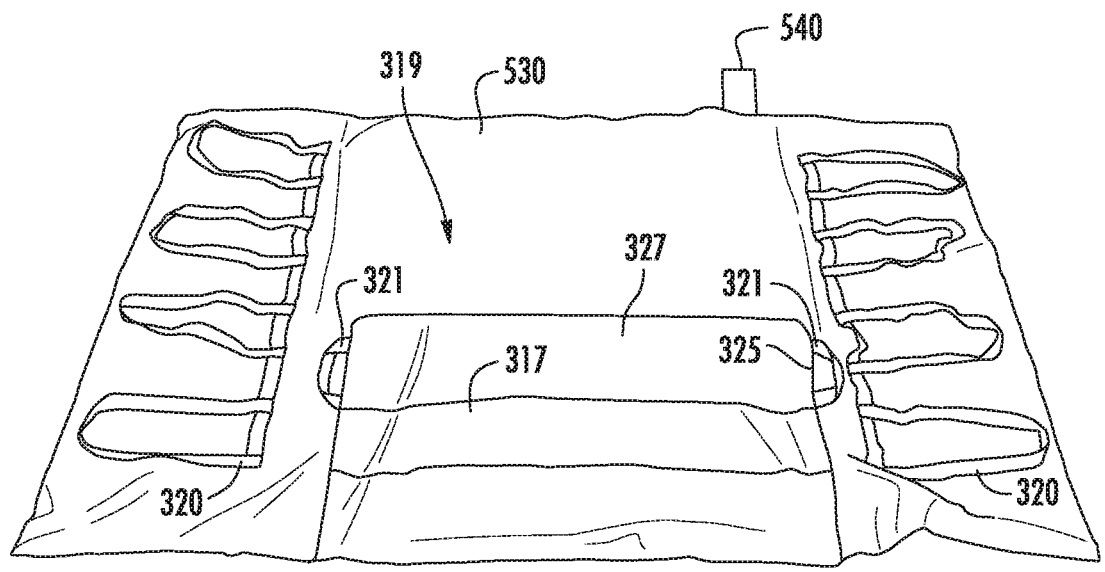
FIG. 21 is a schematic diagram of an outer bladder used in FIG. 18.
Figure 22:
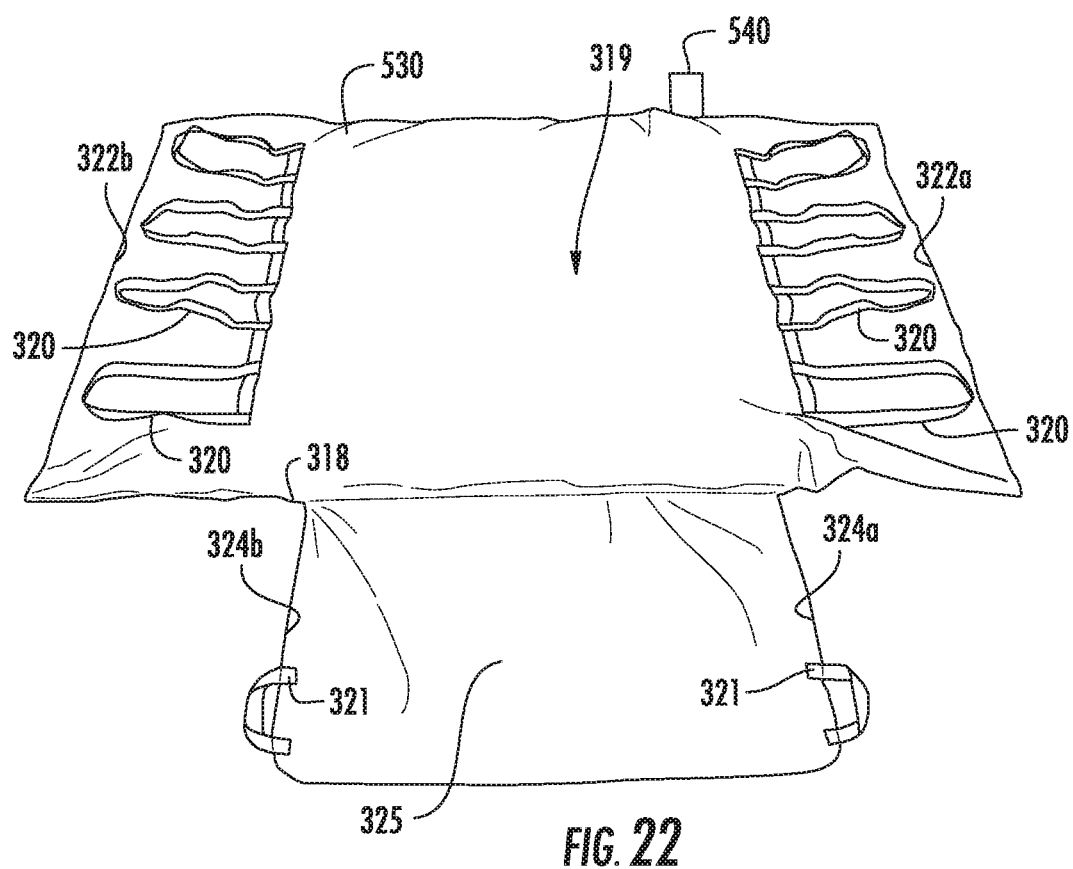
FIG. 22 is a schematic diagram of an outer bladder used in FIG. 18.

Outer bladder 530 can replace first ultra low pressure plenum 312 as shown in FIG. 21 and FIG. 22. Portion 317 on upper surface 327 of extension 325 can be formed of a material having a high coefficient of friction. A suitable material having a high coefficient of friction is a rubberized or non-skid material. Portion 317 can be folded underneath rear surface 319 of outer bladder 530 to prevent movement of outer bladder 530, as shown in FIG. 21. Handles 320 can be provided adjacent either edge 322a, 322b of cover 318 to aid in movement. Handles 321 can be provided adjacent either edge 324a, 324b of extension 325 of cover 318 to aid in folding of extension 325 underneath rear surface 319 as shown in FIG. 22.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A support system for support and off-loading of a received body part comprising:
    a positioner filled with a flowable composition that has no shape memory;
    a first air plenum, the first air plenum consisting of a gas therein, and
    a second air plenum adjacent to the first air plenum, said second air plenum consisting of a gas therein,
    wherein the first and second air plenums comprise bladder portions that are of a substantially similar size and shape and are configured to be placed on top of one another in a planar relationship in use;
    wherein said positioner is adapted to be received under either said first air plenum or said second air plenum, said positioner displaces said gas within said first air plenum and said second air plenum,
    wherein at least one of the first air plenum or the second air plenum comprises an upper bladder and a lower bladder, wherein the lower bladder has a smaller width than the upper bladder such that it forms a tail extension portion, and
    one or more handles associated with the tail extension portion, such that the tail extension portion can be folded underneath the support system.

2. The support system of claim 1 wherein said positioner is adapted to be positioned adjacent the received body part to micro-contour to the received body part and said first air plenum displaces gas in said second air plenum.

3. The system of claim 1 wherein said flowable composition is a fluidized medium composition with a lubricant which flows in response to a deforming pressure and ceases to flow when there is no deforming pressure to provide three dimensional contouring.

4. The system of claim 1 wherein said flowable composition is kinetic sand.

5. The system of claim 1 wherein said flowable composition is a thixotropic plastic.

6. The system of claim 1 wherein said flowable composition is formed of a mixture a lubricant and a material selected from the group comprising beads, polyethylene beads, polystyrene (PS) beads, expanded polyethylene (PE), crosslinked expanded polyethylene (PE), pellets, closed cell foams, microspheres, and encapsulated phase changing materials (PCM), or combinations thereof.

7. The system of claim 1 wherein said pressure within said first air plenum or said second air plenum is a pressure of less than about 500 millibars.

8. The system of claim 1 wherein said first air plenum comprises an upper bladder and a lower bladder, the upper bladder and the lower bladder being in air communication, wherein the lower bladder has a smaller width diameter than the upper bladder.

9. The system of claim 1 wherein a bottom surface of said first air plenum or said second air plenum is formed of a material having a coefficient of friction that is lower than a coefficient of friction of an upper surface of either the first air plenum or the second air plenum.

10. The system of claim 1 wherein an upper surface of said first air plenum or said second air plenum is formed of a material having non-skid properties and wherein a bottom surface of either the first air plenum for the second air plenum is formed of a material that has sliding properties that allow movement of a patient positioned on the system.

11. The system of claim 1 further comprising a base coupled or integral with said first air plenum further comprising gripping handles on either edge of said base.

12. The system of claim 1 further comprising a top layer positioned above said first air plenum, said top layer being coupled to edges of said first air plenum, said top layer comprising a plurality of perforations, and an air source attached through a valve in said top will layer, said air source supplying air beneath said top layer.

13. The system of claim 1 wherein the positioner is a bladder and a pressure within the bladder of the positioner is in a range of less than about 20 mm of water to about 5 mm of water.

14. The system of claim 1, wherein the tail extension portion has an upper surface that is a rubberized or non-skid material.

15. The system of claim 1, wherein a bottom surface of the support system is formed of a material having sliding properties that allows sliding movement of the support system across a hospital bed surface or other patient support surface.

16. A system for support and off-loading of a received body part comprising:
    an inner bladder, said inner bladder being filled with a first flowable composition; and
    an outer bladder positioned adjacent to said inner bladder, said outer bladder being filled with a second flowable composition;
    wherein said first composition has greater flow characteristics than said second composition,
    wherein in use, the inner bladder is positioned adjacent the received body part to micro-contour to the received body part and the outer bladder is positioned external to the inner bladder, such that the inner bladder and the outer bladder are stacked upon one another, and wherein the outer bladder macro-contours to the inner bladder after the inner bladder is micro-contoured to the received body part,
    wherein a bottom surface of the outer bladder is formed of a material having a first coefficient of friction, wherein at least a portion of an upper surface of the inner bladder is formed of a material having a second, higher coefficient of friction, wherein at least a portion of the upper surface of the inner bladder is a rubberized material,
    wherein the rubberized material is positioned on an extension bladder extending from the inner bladder.

17. The system of claim 16, further comprising one or more gripping handles associated with the extension bladder.

18. The system of claim 17, wherein, in use, the extension bladder is folded under the main body, such that the rubberized material is in contact with a hospital bed surface or other patient support surface.

19. The system of claim 16, wherein the material having a first coefficient of friction is a material having sliding properties that allows sliding movement of the system across a hospital bed surface or other patient support surface, and wherein folding the extension bladder under the system causes contact of the rubberized material with the hospital bed surface or other patient support surface, preventing further sliding movement of the system.

20. A system for support and off-loading of a received body part comprising:
   an inner bladder, said inner bladder being filled with a first flowable composition; and
   an outer bladder positioned adjacent to said inner bladder, said outer bladder being filled with a second flowable composition;
   wherein said first composition has greater flow characteristics than said second composition,
   wherein in use, the inner bladder is positioned adjacent the received body part to micro-contour to the received body part and the outer bladder is positioned external to the inner bladder, such that the inner bladder and the outer bladder are stacked upon one another, and wherein the outer bladder macro-contours to the inner bladder after the inner bladder is micro-contoured to the received body part,
   wherein a bottom surface of the outer bladder is formed of a material having a first coefficient of friction, wherein at least a portion of an upper surface of the inner bladder is formed of a material having a second, higher coefficient of friction, wherein at least a portion of the upper surface of the inner bladder is a rubberized material,
   wherein the inner bladder comprises a main body and wherein the rubberized material is positioned on an extension bladder extending from the main body, the extension bladder comprising a width that is smaller than a width of the main body.

* * * * *